US010538785B2

(12) United States Patent
Bauche et al.

(10) Patent No.: US 10,538,785 B2
(45) Date of Patent: Jan. 21, 2020

(54) LYOPHILIZED LENTIVIRAL VECTOR PARTICLES, COMPOSITIONS AND METHODS

(71) Applicants: Cécile Bauche, Paris (FR); Renaud Vaillant, Gentilly (FR)

(72) Inventors: Cecile Bauche, Paris (FR); Gael Ouengue Mbele, Evry (FR)

(73) Assignees: Renaud Vaillant, Gentilly (FR); Cécile Bauche, Paris (FR)

( * ) Notice: Subject to any disclaimer, the term of this patent is extended or adjusted under 35 U.S.C. 154(b) by 0 days.

(21) Appl. No.: 15/106,862

(22) PCT Filed: Dec. 22, 2014

(86) PCT No.: PCT/IB2014/067234
§ 371 (c)(1),
(2) Date: Jun. 21, 2016

(87) PCT Pub. No.: WO2015/097650
PCT Pub. Date: Jul. 2, 2015

(65) Prior Publication Data

US 2017/0037430 A1 Feb. 9, 2017

(30) Foreign Application Priority Data

Dec. 23, 2013 (EP) .................................... 13306831

(51) Int. Cl.

| | |
|---|---|
| ***C12N 15/86*** | (2006.01) |
| ***A61K 48/00*** | (2006.01) |
| ***A61K 9/19*** | (2006.01) |
| ***C12N 7/00*** | (2006.01) |

(52) U.S. Cl.
CPC ................ *C12N 15/86* (2013.01); *A61K 9/19* (2013.01); *A61K 48/0091* (2013.01); *C12N 7/00* (2013.01); *C12N 2740/16043* (2013.01); *C12N 2740/16051* (2013.01)

(58) Field of Classification Search
None
See application file for complete search history.

(56) References Cited

U.S. PATENT DOCUMENTS

| | | | |
|---|---|---|---|
| 5,661,022 | A | 8/1997 | Kotani et al. |
| 2014/0271715 | A1 | 9/2014 | Stinchcomb et al. |
| 2015/0030629 | A1 | 1/2015 | De Staat Der Nederlanden |
| 2015/0265688 | A1 | 9/2015 | Cigarini |

FOREIGN PATENT DOCUMENTS

| | | | |
|---|---|---|---|
| CA | 297434 | A1 | 4/2015 |
| CN | 103690943 | A | 4/2014 |
| CN | 105233296 | A | 1/2016 |
| CN | 106237339 | A | 12/2016 |
| CN | 106492213 | A | 3/2017 |
| EP | 2 385 107 | A1 | 11/2011 |
| EP | 3127550 | A1 | 8/2017 |
| WO | 2013/076309 | A1 | 5/2013 |
| WO | 2017041083 | A1 | 3/2017 |
| WO | 2017047089 | A1 | 3/2017 |
| WO | 2017172643 | A1 | 10/2017 |

OTHER PUBLICATIONS

Zimmerman, et al. (2011) "Highly efficient concentration of lenti- and retroviral vector preparations by membrane adsorbers and ultrafiltration", BMC Biotechnology, 11:55 (12 pages).*
Delacroix, et al. (2015) "Development of a Successful Lyophilization Process for Lentiviral Vector Clinical Batches", Molecular Therapy, 23(Suppl 1), Presentation Abstract No. 671, p. S267.*
Hansen, et al. (2015) "Freeze-drying of live virus vaccines: A review", Vaccine, 33: 5507-19.*
Shin et al.; "Lentivirus delivery by absorption to tissue engineering scaffolds"; Journal of Biomedical Materials Research Part A, vol. 9999A, No. 4, Jun. 15, 2009, pp. 1252-1259.
Mather et al.; "Lyophilisation of influenza, rabies and Marburg lentiviral pseudotype viruses for the development and distribution of a neutralisation-assay-based diagnostic kit"; Journal of Virological Methods, vol. 210, Oct. 5, 2014, pp. 51-58.
Cruz et al.; "Screening of Novel Excipients for Improving the Stability of Retroviral and Adenoviral Vectors"; Biotechnology Progress, vol. 22, No. 2, Apr. 7, 2006, pp. 568-576.
Coutant et al.; "A Nonintegrative Lentiviral Vector-Based Vaccine Provides Long-Term Sterile Protection against Malaria"; PLOS One, vol. 7, No. 11, Nov. 2, 2012, pp. 1-14.
Bauche et al.; Manufacturing of Lentiviral Based Viral Vectored Vaccine, From Benchmark to HIV Phase I/II Clinical Trial; Molecular Therapy, vol. 22, No. suppl May 1, 2014, p. S285.
Bauche et al.; "Lentiviral-Based Anti-HIV Therapeutic Vaccine: Design, Preclinical Studies and PhaseI/II Clinical Trial Preliminary Results"; Molecular Therapy, vol. 22, No. suppl May 1, 2014, pp. S269.
Jamil, R.K., et. al., "Evaluation of the thermal stability of a novel strain of live-attenuatedmumps vaccine (RS-12 strain) lyophilized in different stabilizers", (J Virol Methods. Apr. 2014; 199:35-8).
Stewart, M., et. al., "Use of adenovirus as a model system to illustrate a simple methodusing standard equipment and inexpensive excipients to remove livevirus dependence on the cold-chain", (Vaccine, May 19, 2014; 32(24)2931-8).
Prabhu M., et. al., "Evaluation of stability of live attenuated camelpox vaccine stabilized with different stabilizers and reconstituted with various diluents", (Biologicals, May 2014; 42(3) 169-75.).

(Continued)

*Primary Examiner* — Robert M Kelly
(74) *Attorney, Agent, or Firm* — Posternak, Blankstein & Lund LLP

(57) ABSTRACT

Methods of making lyophilized lentiviral vector particles are provided. Compositions comprising lyophilized lentiviral vector particles are also provided. Methods of administering a lentiviral vector particle to a subject and uses of lentiviral vector particle compositions are also provided.

25 Claims, 15 Drawing Sheets

Specification includes a Sequence Listing.

(56) References Cited

OTHER PUBLICATIONS

Ghobadloo, S.M., et. al., "Aptamer-Facilitated Cryoprotection of Viruses," (ACS Med Chem. Lett. Nov. 13, 2014; 5 (11) 1240-1244).
Pelliccia, M. et. al., "Additives for vaccine storage to improve thermal stability of adenoviruses from hours to months," (Nat. Commun. 2016; 7: 13520).
XI, Wei, et. al., "Preparation of lyophilized lentiviral vector of bone morphogenetic protein 2," (Shanghai Kou Qiang Yi Xue. Oct. 2015; 24(5):525-9).

* cited by examiner

| | | | | | |
|---|---|---|---|---|---|
| | | 165-14-0288 | | 165-14-0293 | |
| | | Sucrose - | | Sucrose + | |
| | | IEX 1 | IEX 2 | IEX 1 | IEX 2 |
| Bulk | Infectious Titer (TU/ml) | **2E+07** | | **2E+07** | |
| Epool | Infectious Titer (TU/ml) | **2,59E+07** | **3,09E+07** | **3,5E+07** | **3,6E+07** |
| | Recovery (%) | #50% | #60% | #60% | #60% |

| | | 165-14-0288 | | 165-14-0293 | |
|---|---|---|---|---|---|
| | | A (Sucros e- / HSA -) | B (Sucrose - /HSA +) | C (Sucrose + / HSA -) | D (Sucrose + / HSA+) |
| **FORMULATION S0 (20 mM Tris pH7,6 ; MgCl2 2 mM ; Sucrose 0,05 M)** | | | | | |
| Frozen | Infectious Titer (TU/ml) | 6,64E+05 | 1,37E+06 | 4,92E+05 | 7,36E+05 |
| Lyophilized | Infectious Titer (TU/ml) | 3,38E+05 | 7,30E+05 | 1,94E+05 | 3,04E+05 |
| **FORMULATION S1 (20 mM Tris pH7,6 ; MgCl2 2 mM ; Sucrose 0,5 M)** | | | | | |
| Frozen | Infectious Titer (TU/ml) | 1,44E+06 | 2,11E+06 | 1,20E+06 | 1,99E+06 |
| Lyophilized | Infectious Titer (TU/ml) | 1,28E+05 | 7,91E+05 | 5,28E+04 | 3,32E+05 |

FIGURE 12

| | | | |
|---|---|---|---|
| | | 165-14-0310 | |
| | | Sucrose - | |
| | | IEX 1 | IEX 2 |
| Bulk traité | Infectious Titer (TU/ml) | 4E+07 | |
| Epool HSA 0 / +4°_ OV (A) | Infectious Titer (TU/ml) | 3,7E+07 | |
| UF HSA 0 (A) | Infectious Titer (TU/ml) | 2,38E+08 | |
| Epool HSA 0,01% / +4°_ OV (A) | Infectious Titer (TU/ml) | 3,12E+07 | |
| UF HSA 0,01% (A) | Infectious Titer (TU/ml) | 3,04E+08 | |

FIGURE 13

| N°Assay | Condition | Identity | Titer (TU/mL) | Residual DNA | HSA $mg.mL^{-1}$ | HCP $ng.mL^{-1}$ |
|---|---|---|---|---|---|---|
| | | | | | | |
| 165-14-0310 | Frozen A S0 | UF- HSA 0 / Dil_Sucrose 0 | 8,43E+07 | 156,16 | - | 472,09 |
| 165-14-0310 | Frozen A S1 | UF- HSA 0 / Dil_Sucrose 0,5M | 1,19E+08 | 127,35 | - | 431,71 |
| 165-14-0310 | Lyo A S0 | UF- HSA 0 / Dil_Sucrose 0 | 7,22E+07 | 108,09 | - | 450,13 |
| 165-14-0310 | Lyo A S1 | UF- HSA 0 / Dil_Sucrose 0,5M | 7,89E+07 | 88,15 | - | 428,28 |
| | | | | | | |
| 165-14-0310 | Frozen B S0 | UF- HSA + / Dil_Sucrose 0 | 1,46E+08 | 159,46 | 9,61 | 517,07 |
| 165-14-0310 | Frozen B S1 | UF- HSA + / Dil_Sucrose 0,5M | 1,88E+08 | 158,20 | 8,88 | 473,00 |
| 165-14-0310 | Lyo B S0 | UF- HSA + / Dil_Sucrose 0 | 1,17E+08 | 188,19 | 9,40 | 523,92 |
| 165-14-0310 | Lyo B S1 | UF- HSA + / Dil_Sucrose 0,5M | 1,41E+08 | 156,33 | 8,66 | 459,58 |

FIGURE 14

LYOPHILIZED LENTIVIRAL VECTOR PARTICLES, COMPOSITIONS AND METHODS

FIELD OF THE INVENTION

The present invention is in the field of lentiviral vector technology and relates to new and useful lyophilized lentiviral vector particles, methods of making lyophilized lentiviral vector particles, and methods of using lyophilized lentiviral vector particles, among other things.

INTRODUCTION

Retroviral vectors deriving from lentivirus genomes (i.e. lentiviral vectors) have emerged as promising tools for both gene therapy and immunotherapy purposes, because they exhibit several advantages over other viral systems. In particular, lentiviral vectors themselves are not toxic and, unlike other retroviruses, lentiviruses are capable of transducing non-dividing cells, in particular dendritic cells (He et al. 2007, Expert Rev vaccines, 6(6):913-24), allowing stable transduction and antigen presentation through the endogenous pathway.

Lentiviruses are linked by similarities in genetic composition, molecular mechanisms of replication and biological interactions with their hosts. They are best known as agents of slow disease syndromes that begin insidiously after prolonged periods of subclinical infection and progress slowly; thus, they are referred to as the "slow" viruses (Narayan et al., 1989, J Gen Virol, 70(7):1617-39). They have the same basic organization as all retroviruses but are more complex due to the presence of accessory genes (e.g., vif, vpr, vpu, nef, tat, and rev), which play key roles in lentiviral replication in vivo.

Lentiviruses represent a genus of slow viruses of the Retroviridae family, which includes the human immunodeficiency viruses (HIV), the simian immunodeficiency virus (SIV), the equine infectious encephalitis virus (EIAV), the caprine arthritis encephalitis virus (CAEV), the bovine immunodeficiency virus (BIV) and the feline immunodeficiency virus (FIV). Lentiviruses can persist indefinitely in their hosts and replicate continuously at variable rates during the course of the lifelong infection. Persistent replication of the viruses in their hosts depends on their ability to circumvent host defenses.

Following production, lentiviral vector particles for therapeutic uses must be formulated, stored, and transported to a site where they will be administered to a subject. It is important that this process maintains the stability of the lentiviral vector particles in order to allow for a predictable efficacy and safety profile, for example, while at the same time not incorporating components into the formulation that are incompatible with therapeutic administration.

Lyophilisation (or Freeze-Drying) is a formulation approach used in the pharmaceutical industry for the stabilisation of products. However, during freezing and subsequent drying, the product is exposed to diverse stress factors which can cause significant loss of activity.

Several factors have been shown to have unpredictable effects on stability of lyophilized viruses. For example, during freezing, drug stability can also be influenced by exposure to ice-water interfaces, pH shifts due to selective crystallization of buffer species, and mechanical damage by growing ice crystals. During drying, removal of stabilizing hydration shells can also influence stability. These and other factors make it unpredictable whether any particular set of conditions will be compatible with lyophilization of a particular type of virus.

Cruz et al., 2006, Biotechnol Prog., 22(2):568-576 produced Moloney Monkey Leukemia Virus-based vectors coding the LacZ gene. The vectors were obtained from packaging cell supernatant treated by ultracentrifugation. The vectors were then lyophilized in sucrose, trehalose, firoin, or ectoin. Cruz also produced adenoviral vectors for lyophilization using CsCl gradient centrifugation. Neither technique is suitable to purify lentiviral vectors to the extent required for pharmaceutical applications. Both techniques produce viral vector products containing unacceptable levels of contaminants. While those contaminants are incompatible with lentiviral pharmaceutical applications, the contaminants likely contribute to stabilizing the viral vectors in the lyophilized compositions produced by Cruz. For these reasons the methods of Cruz are unsuitable for production of pharmaceutical grade lentiviral vector compositions. Thus, Cruz does not teach how to lyophilize formulations of lentiviral vector particles suitable for pharmaceutical applications.

Shin et al., (2010. J. Biomed) described lyophilization of unpurified and unconcentrated lentiviral preparations in the presence of polyethylene glycol (PEG) and 10% FBS. Shin et al. used the PEG-it™ system for lentiviral purification, which is expressly not designed for use in humans and used PLG scaffolds. Thus, the lyophilized viral material contained serum albumin present in the cellular supernatant from which the virus was obtained and also PEG. Both components are incompatible with lentiviral vector formulations for pharmaceutical applications. While those contaminants are incompatible with lentiviral pharmaceutical applications, the contaminants likely contribute to stabilizing the viral vectors in the lyophilized compositions produced by Shin. For these reasons the methods of Shin are unsuitable for production of pharmaceutical grade lentiviral vector compositions. Thus, Shin does not teach how to lyophilize formulations of lentiviral vector particles, as well as formulations in solution, suitable for pharmaceutical applications.

Accordingly, there is a need in the art for new methods of making lyophilized lentiviral vector particles and for compositions comprising lyophilized lentiviral particles that are suitable for administration to a human subject, for example as a pharmaceutical. The present invention meets these and other needs.

SUMMARY OF THE INVENTION

The invention encompasses methods for making lyophilized lentiviral vector particles. In one embodiment, the method comprises:

a) providing a cell supernatant comprising lentiviral vector particles, b) purifying the lentiviral vector particles in the supernatant, c) concentrating the purified lentiviral vector particles, d) freezing the concentrated lentiviral vector particles to provide frozen lentiviral vector particles, e) lyophilizing the frozen lentiviral vector particles to provide lyophilized lentiviral vector particles, and f) storing the lyophilized lentiviral vector particles for at least three days.

In one embodiment, the provided cell supernatant does not comprise serum albumin. In one embodiment, the concentrated lentiviral vector particles are frozen in the presence of no more than 0.1% non-human serum albumin. In one embodiment, the concentrated lentiviral vector particles are frozen in the presence of no more than 0.01% non-human serum albumin. In one embodiment, the concentrated lentiviral vector particles are frozen in the absence of non-human serum albumin. In one embodiment, the concentrated lentiviral vector particles are frozen in the presence of no more than 0.1% serum albumin. In one embodiment, the concentrated lentiviral vector particles are frozen in the presence of no more than 0.01% serum albumin.

In one embodiment, the concentrated lentiviral vector particles are frozen in the presence of a lyoprotectant. In one embodiment,the purifying and concentrating occurs in the absence of polyethylene glycol.

In one embodiment,the concentrated lentiviral vector particles produced in c) comprise no more than 1 μg total DNA per $1\times10^8$ TU.

In one embodiment,concentrating the purified lentiviral vector particles is performed without centrifugation. In one embodiment, concentrating the purified lentiviral vector particles is performed in the absence of polyethylene glycol.

In one embodiment,the concentrated lentiviral vector particles produced in c) comprise no more than 20 μg of serum albumin per $1\times10^8$ TU.

In one embodiment, the concentrated lentiviral vector particles produced in c) comprise an infectious titer of at least at least $1\times10^7$ TU/mL. In one embodiment, concentrated lentiviral vector particles produced in c) comprise an infectious titer of at least $1\times10^8$ TU/mL.

In one embodiment, purifying in b) comprises clarifying the cell supernatant of a), and wherein the amount of total DNA per TU present in the concentrated lentiviral vector particles produced in c) is no more than 20% of the amount of total DNA per TU present in the cell supernatant. In one embodiment, purifying in b) comprises clarifying the cell supernatant of a), and wherein the amount of total protein per TU present in the concentrated lentiviral vector particles produced in c) is no more than 1% of the amount of total protein per TU present in the cell supernatant.

In one embodiment, purifying in b) comprises clarifying the cell supernatant of a), and wherein the amount of host cell proteins per TU present in the concentrated lentiviral vector particles produced in c) is no more than 1% of the amount of total host cell proteins per TU present in the cell supernatant.

In one embodiment, the lyoprotectant is at least one of at least one sugar and at least one polyalcohol. In one embodiment, the purified and concentrated lentivirus composition is frozen in the presence of at least 0.25 M lyoprotectant. In one embodiment, the purified and concentrated lentivirus composition is frozen in the presence of from 0.25 M to 1 M lyoprotectant. In one embodiment, at least one sugar is selected from sucrose and trehalose.

In one embodiment,lyophilized lentiviral vector particles are stored for from 7 to 45 days. In one embodiment, the lyophilized lentiviral vector particles are stored at from −1° C. to 9° C. In one embodiment, the lyophilized lentiviral vector particles are stored at from −25° C. to −15° C. In one embodiment, lentiviral particle titer after storing is at least 80% of the lentiviral particle titer after freezing and before lyophilizing.

The invention encompasses lyophilized lentiviral particles made by the methods of the invention. Thus, the invention encompasses a lyophilized composition comprising lentiviral vector particles and no more than 20 μg of serum albumin per $1\times10^8$ TU of lentiviral vector particles in the composition. In one embodiment, the composition comprises no more than 0.1% non-human serum albumin. In one embodiment, the composition comprises no more than 0.01% non-human serum albumin. In one embodiment, the composition does not comprise non-human serum albumin. In one embodiment, the composition comprises no more than 0.1% serum albumin. In one embodiment, the composition comprises no more than 0.01% serum albumin.

In one embodiment, the composition does not comprise polyethylene glycol. In one embodiment, the composition comprises at least one lyoprotectant. In one embodiment, lyoprotectant is at least one of at least one sugar and at least one polyalcohol. In one embodiment, at least one sugar is selected from sucrose and trehalose.

In one embodiment, the lentiviral particles are reconstituted in the freeze volume the infectious titer of the composition is at least $1\times10^6$ TU/mg. In one embodiment, the composition has been stored in lyophilized form for at least 3 days. In one embodiment, the composition has been stored in lyophilized form for from 7 to 45 days.

In one embodiment, the composition has been stored in lyophilized form at from −1° C. to 9° C. In one embodiment, the composition has been stored in lyophilized form at from −25° C. to −15° C.

The invention encompasses methods of administering a lentiviral vector particle to a human subject. In one embodiment, the method comprises:

providing a lyophilized composition comprising lentiviral vector particles;

reconstituting the lyophilized composition comprising lentiviral vector particles in an aqueous medium for administration; and administering the reconstituted lentiviral vector particles to the human subject;

wherein the lyophilized composition comprising lentiviral vector particles containing no more than 20 μg serum albumin per 1×108 TU of lentiviral vector particles in the composition.

In one embodiment, the lyophilized composition comprising lentiviral vector particles comprises no more than 0.1% non-human serum albumin. In one embodiment, the lyophilized composition comprising lentiviral vector particles comprises no more than 0.01% non-human serum albumin. In one embodiment, the lyophilized composition comprising lentiviral vector particles does not comprise non-human serum albumin. In one embodiment, the lyophilized composition comprising lentiviral vector particles comprises no more than 0.1% serum albumin. In one embodiment, the lyophilized composition comprising lentiviral vector particles comprises no more than 0.01% serum albumin.

In one embodiment, the invention comprises:

a) making lyophilized lentiviral vector particles by a method comprising:

i) providing a cell supernatant comprising lentiviral vector particles, ii) purifying the lentiviral vector particles in the supernatant, iii) concentrating the purified lentiviral vector particles, iv) freezing the concentrated lentiviral vector particles to provide frozen lentiviral vector particles, v) lyophilizing the frozen lentiviral vector particles to provide lyophilized lentiviral vector particles, and vi) storing the lyophilized lentiviral vector particles for at least three days;

b) reconstituting the lyophilized lentiviral vector particles in an aqueous medium for administration; and c) administering the reconstituted lentiviral vector particles to the human subject.

In one embodiment, the provided cell supernatant does not comprise non-human serum albumin. In one embodiment, the concentrated lentiviral vector particles are frozen in the presence of no more than 0.1% non-human serum albumin. In one embodiment, the concentrated lentiviral vector particles are frozen in the presence of no more than 0.01% serum albumin. In one embodiment, the concentrated lentiviral vector particles are frozen in the presence of a lyoprotectant. In one embodiment, the lyophilized lentiviral vector particles comprise no more than 20 μg of serum albumin per 1×108 TU of lentiviral vector particles in the composition. In one embodiment, the lyophilized lentiviral vector particles do not comprise non-human serum albumin.

The invention encompasses the use of a lyophilized composition comprising lentiviral vector particles for administering a lentiviral vector particle to a subject, wherein the lyophilized composition comprising lentiviral vector particles comprises no more than 20 μg of serum albumin per $1\times10^8$ TU of lentiviral vector particles in the composition.

BRIEF DESCRIPTION OF THE DRAWINGS

FIG. 12. Effect of Lyophilization+/−sucrose and +/−HSA. Infectious titers were determined in frozen vs. frozen and lyophilized samples+/−sucrose and +/−HSA.

FIG. 13. Infectious titers recovered at each step. Infectious titers were determined at the indicated steps+/−HSA.

FIG. 14. Neither sucrose nor serum albumin are required for infectious lyophilized lentiviral vectors. Infectious titers were determined in frozen vs. frozen and lyophilized samples+/−sucrose and +/−HSA.

DETAILED DESCRIPTION

Figure 1A:
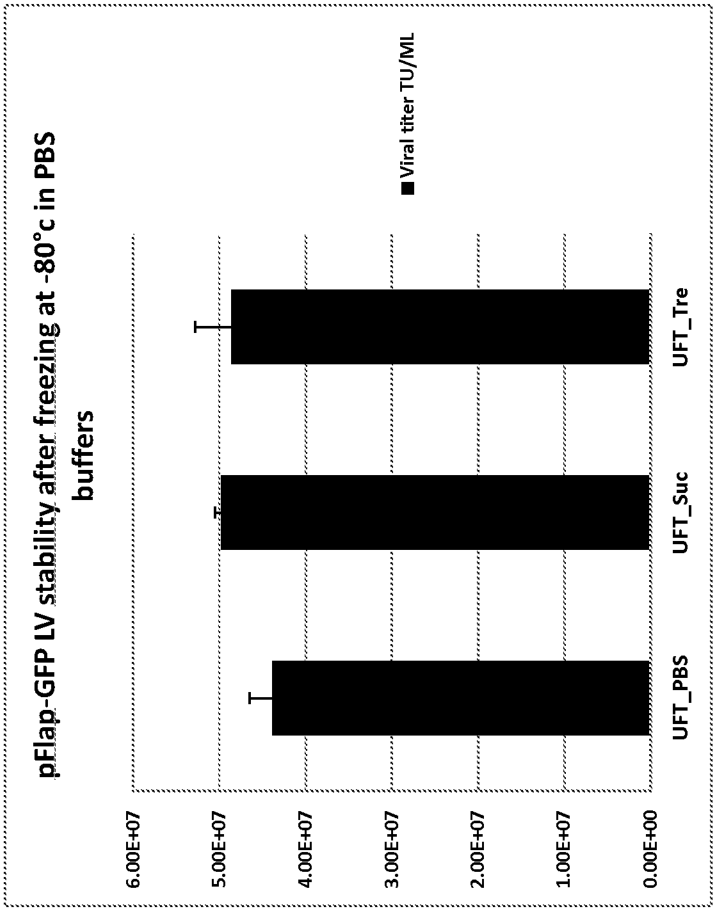
FIGS. 1A and 1B. Choice of buffer for lentiviral vector freezing. After purification through Anion-exchanger Q-mustang chromatography, the collected peak fractions were concentrated using Ultrafiltration/Diafiltration techniques, with either PBS/Lactose 40 mg/L or 20 mM Tris pH 7.5/$MgCl_2$ 2 mM/Lactose 40 mg/L buffers.

The inventors have discovered new and useful methods of making lyophilized compositions comprising lentiviral vector particles. As shown in the examples, the methods may be used to make lyophilized lentiviral vector particles from suspensions of lentiviral vector particles that comprise a high infectious titer and a low level of at least one of total residual DNA, total protein, host cell protein, and residual serum albumin. In some embodiments the lyophilized lentiviral vector particles comprise no more than 0.1% serum albumin. In some embodiments the lyophilized lentiviral vector particles comprise no more than 0.01% serum albumin. In some embodiments the lyophilized lentiviral vector particles do not comprise serum albumin. In some embodiments the lyophilized lentiviral vector particles are made from suspensions of lentiviral vector particles suitable for pharmaceutical administration to a subject to in turn make lyophilized lentiviral vector particles suitable for administration to a subject. As further shown in the examples, the inventors have found that such lyophilized lentiviral particle compositions are highly stable over a useful timeframe when stored. Based in part on these and other discoveries the inventors provide new and useful methods and compositions herein.

Definitions

For the purposes of interpreting of this specification, the following definitions will apply and whenever appropriate, terms used in the singular will also include the plural and vice versa. In the event that any definition set forth below conflicts with the usage of that word in any other document, the definition set forth below shall always control for purposes of interpreting the scope and intent of this specification and its associated claims. Notwithstanding the foregoing, the scope and meaning of any document incorporated herein by reference should not be altered by the definition presented below. Rather, said incorporated document should be interpreted as it would be by the ordinary practitioner based on its content and disclosure with reference to the content of the description provided herein.

The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising" "include," "includes," and "including" are interchangeable and not intended to be limiting. Furthermore, where the description of one or more embodiments uses the term "comprising," those skilled in the art would understand that in some specific instances, the embodiment or embodiments can be alternatively described using language "consisting essentially of" and/or "consisting of."

As used herein the term "subject" refers to any animal subject including laboratory animals (e.g., primates, rats, mice), livestock (e.g., cows, sheep, goats, pigs, turkeys, chickens), household pets (e.g., dogs, cats, rodents, etc.), and humans.

As used herein "lyophilization" refers to a freezedrying process in which a material is frozen and then the surrounding pressure is reduced to allow the frozen water in the material to sublimate directly from the solid phase to the gas phase. In lyophilized compositions according to this disclosure lyophilization results in formation of a lyophilized composition. Typically a lyophilized composition according to the invention comprises no more than 10% residual water. For example, in some embodiments the lyophilized composition comprises no more than 10%, no more than 9%, no more than 8%, no more than 7% no more than 6%, no more than 5%, no more than 4%, no more than 3%, no more than 2%, or no more than 1% residual water. In some embodiments the lyophilized composition comprises from 1% to 2% residual water, from 1% to 3% residual water, from 1% to 4% residual water, or from 1% to 5% residual water.

As used herein "lyoprotectant" is a molecule that protects freeze-dried material. Lyoprotectants are typically (but not exclusively) polyhydroxy compounds such as sugars (mono-, di-, and polysaccharides), polyalcohols, and their derivatives. Nonlimiting examples of lyoprotectants are carborhydrate lyoprotectants as such as sucrose, glucose, lactose, trehalose, arabinose, pentose, ribose, xylose, galactose, hexose, idose, monnose, talose, heptose, fructose, gluconic acid, sorbitol, (mannitol), methyl [alpha]-glucopyranoside, maltose, isoascorbic acid, ascorbic acid, lactone, sorbose, glucaric acid, erythrose, threose, arabinose, allose, altrose, gulose, erythrulose, ribulose, xylulose, psicose, tagatose, glucuronic acid, gluconic acid, glucaric acid, galacturonic acid, mannuronic acid, glucosamine, galactosamine, neuraminic acid, arabinans, fructans, fucans, galactans, galacturonans, glucans, mannans, xylans, levan, fucoidan, carrageenan, galactocarolose, pectins, pectic acids, amylose, pullulan, glycogen, amylopectin, cellulose, dextran, pustulan, chitin, agarose, keratin, chondroitin, dermatan, hyaluronic acid, alginic acid, xanthin gum, starch and combinations of two or more thereof.

As used herein a "supernatant" is the liquid portion of a cell culture after the cells are removed. In the case of a cell culture comprising cells attached to a solid substrate the cells my be removed from the liquid by transferring the liquid to a different container, for example. In the case of a suspension culture the cells may be removed using centrifugation and/or filtration, for example.

Lentiviral Vector Particles

Within the context of this invention, a "lentiviral vector" means a non-replicating vector for the transduction of a host cell with a transgene comprising cis-acting lentiviral RNA or DNA sequences, and requiring lentiviral proteins (e.g., Gag, Pol, and/or Env) that are provided in trans. The lentiviral vector lacks expression of functional Gag, Pol, and Env proteins. The lentiviral vector may be present in the form of an RNA or DNA molecule, depending on the stage of production or development of said retroviral vectors.

The lentiviral vector can be in the form of a recombinant DNA molecule, such as a plasmid. The lentiviral vector can be in the form of a "lentiviral vector particle" such as an RNA molecule(s) within a complex of lentiviral and other proteins. Typically, lentiviral vector particles, which correspond to modified or recombinant lentivirus particles, comprise a genome which is composed of two copies of single-stranded RNA. These RNA sequences can be obtained by transcription from a double-stranded DNA sequence inserted into a host cell genome (proviral vector DNA) or can be obtained from the transient expression of plasmid DNA (plasmid vector DNA) in a transformed host cell.

Typically the lentiviral vector particles have the capacity for integration. As such, they contain a functional integrase protein. Non-integrating vector particles have one or more mutations that eliminate most or all of the integrating capacity of the lentiviral vector particles. For, example, a non-integrating vector particle can contain mutations in the integrase encoded by the lentiviral pol gene that cause a reduction in integrating capacity. In contrast, an integrating vector particle comprises a functional integrase protein that does not contain any mutations that eliminate most or all of the integrating capacity of the lentiviral vector particles.

Lentiviral vectors derive from lentiviruses, in particular human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV), which are modified to remove genetic determinants involved in pathogenicity and introduce new determinants useful for obtaining therapeutic effects.

Such vectors are based on the separation of the cis- and trans-acting sequences. In order to generate replication-defective vectors, the trans-acting sequences (e.g., gag, pol, tat, rev, and env genes) can be deleted and replaced by an expression cassette encoding a transgene.

Efficient integration and replication in non-dividing cells generally requires the presence of two cis-acting sequences at the center of the lentiviral genome, the central polypurine tract (cPPT) and the central termination sequence (CTS). These lead to the formation of a triple-stranded DNA structure called the central DNA “flap”, which acts as a signal for uncoating of the pre-integration complex at the nuclear pore and efficient importation of the expression cassette into the nucleus of non-dividing cells, such as dendritic cells.

In some embodiments the invention encompasses a lentiviral vector comprising a central polypurine tract and central termination sequence referred to as cPPT/CTS sequence as described, in particular, in the European patent application EP 2 169 073.

Figure 1B:
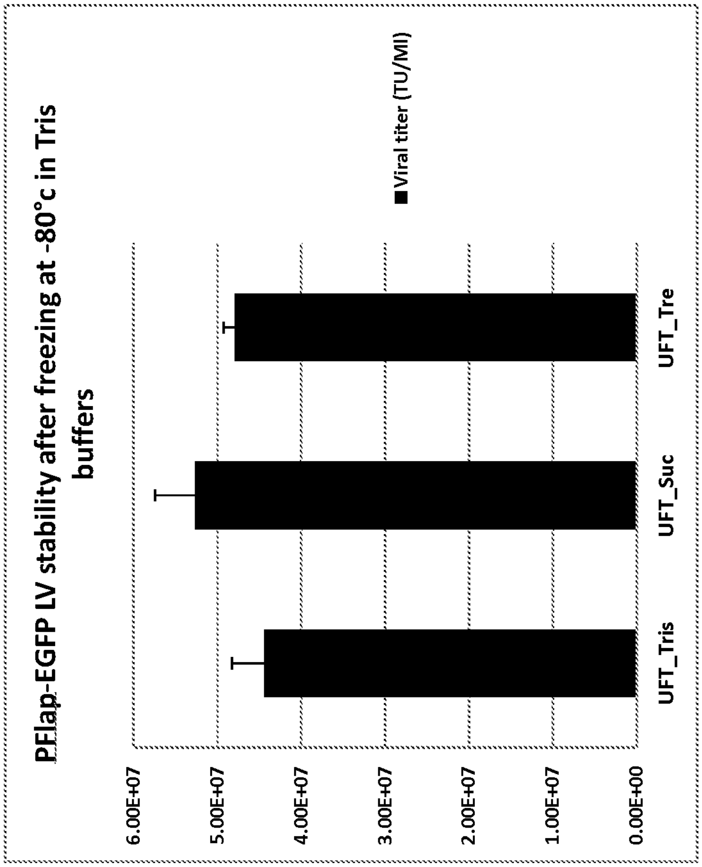

Further sequences are usually present in cis, such as the long terminal repeats (LTRs) that are involved in integration of the vector proviral DNA sequence into a host cell genome. Vectors may be obtained by mutating the LTR sequences, for instance, in domain U3 of said LTR (ΔU3) (Miyoshi H et al, 1998, *J Virol.* 72(10):8150-7; Zufferey et al., 1998, *J Virol* 72(12):9873-80) as shown in FIG. 1.

Typically the vector does not contain an enhancer. In one embodiment, the invention encompasses a lentiviral vector comprising LTR sequences, preferably with a mutated U3 region (ΔU3) removing promoter and enhancer sequences in the 3' LTR.

The packaging sequence Ψ (psi) can also be incorporated to help the encapsidation of the polynucleotide sequence into the vector particles (Kessler et al., 2007, *Leukemia,* 21(9):1859-74; Paschen et al., 2004, *Cancer Immunol Immunother* 12(6):196-203).

In some embodiments, the invention encompasses a lentiviral vector comprising a lentiviral packaging sequence Ψ (psi).

Further additional functional sequences, such as a transport RNA-binding site or primer binding site (PBS) or a Woodchuck PostTranscriptional Regulatory Element (WPRE), can also be advantageously included in the lentiviral vector polynucleotide sequence of the present invention, to obtain a more stable expression of the transgene in vivo.

Methods of Making Lyophilized Lentiviral Particles

The invention encompasses methods of making lyophilized lentiviral particles. In some embodiments, the method comprises a) providing a cell supernatant comprising lentiviral vector particles, b) purifying the lentiviral vector particles in the supernatant, c) concentrating the purified lentiviral vector particles, d) freezing the concentrated lentiviral vector particles to provide frozen lentiviral vector particles, and e) lyophilizing the frozen lentiviral vector particles to provide lyophilized lentiviral vector particles. In step d) the concentrated lentiviral vector particles may optionally be frozen in the presence of a lyoprotectant. The methods may optionally further comprise f) storing the lyophilized lentiviral vector particles.

In some embodiments, the method comprises a) providing concentrated and purified lentiviral vector particles, b) freezing the concentrated lentiviral vector particles to provide frozen lentiviral vector particles, and c) lyophilizing the frozen lentiviral vector particles to provide lyophilized lentiviral vector particles. Preferably, the concentrated and purified lentiviral vector particles are obtained from a cell culture grown in media without added non-human serum. In one embodiment, the concentrated and purified lentiviral vector particles comprise human serum albumin, preferably at a concentration of at least 0.1, 0.2, 0.5, 1, 2, 3, 4, 5, 6, 7, 8, 9, or 10 mg/ml. In one embodiment, the concentrated and purified lentiviral vector particles do not comprise any human or non-human serum albumin.

Most preferably, the lyophilized lentiviral vector particles are not attached to a substrate or scaffold.

The methods can further comprise administering the lyophilized lentiviral vector particles to a human subject.

The cell supernatant is typically obtained from a culture of cells that produces lentiviral particles. In some embodiments all or some of the cells in the culture may be attached to a solid support when the supernatant is obtained. In some embodiments all or some of the cells in the culture are growing in suspension when the supernatant is obtained. The lentiviral particles can be produced by recombinant technology upon transient transfection of cells, for example HEK 293T human cultured cells, by different DNA plasmids. For example, one combination of plasmids that may be used is (i) a packaging plasmid, which expresses at least the Gag, Pol Rev, Tat and, in some cases, structural and enzymatic proteins necessary for the packaging of the transfer construct; (ii) a proviral transfer plasmid, containing an expression cassette and HIV cis-acting factors necessary for packaging, reverse transcription, and integration; and (iii) an envelope-encoding plasmid, in most cases the glycoprotein of vesicular stomatitis virus (VSV.G), a protein that allows the formation of mixed particles (pseudotypes) that can target a wide variety of cells, especially major histocompatibility (MHC) antigen-presenting cells (APCs), including DCs.

This procedure allows obtaining transient production of lentiviral particle vectors by the transfected cells. However, the lentiviral particle vectors may also be continuously produced by cells by stably inserting the packaging genes, the proviral coding DNA, and the envelope gene into the cellular genome. This allows the continuous production of lentiviral particle vectors by the cells without the need for transient transfection. Of course, a combination of these procedures can be used, with some of the DNAs/plasmids integrated into the cellular genome and others provided by transient transfection. Skilled artisans appreciate that several different methods and reagents may be used to make lentiviral vector particles.

In both methods using transiently transfected cells and methods using cells comprising stably inserted packaging genes, proviral coding DNA, and envelope gene, methods typically comprise culturing the cells producing the lentiviral vector particles in culture medium for a period of time, and then collecting the culture media to provide a cell supernatant comprising lentiviral vector particles. In some embodiments the culture medium that is used does not comprise serum albumin. For example, cells may first be cultured in medium that does comprise serum albumin and then switched to medium that does not comprise serum albumin for production of lentiviral vector particles that will be collected. In embodiments utilizing transient transfection the switch to medium that does not comprise serum proteins may occur (before, at the same time as, or after) transfection.

In some embodiments the culture medium used for production of lentiviral vector particles does comprise non-human serum, for example at a concentration of less than 1%, 2%, 3%, 4%, 5%, 6%, 7%, 8%, 9% or 10% non-human serum. In such embodiments that is culture media to provide a cell supernatant comprising lentiviral vector particles. In such embodiments, the concentration of serum albumin may be reduced during the b) purifying the lentiviral vector particles in the supernatant and/or c) concentrating the purified lentiviral vector particles steps of the methods.

Purification may comprise any suitable methods known in the art that reduces the concentration of at least one contaminant in the lentiviral composition relative to the concentration of lentiviral vector particles in the composition (typically measured as an infectious titer of lentiviral particles and/or a physical titer of lentiviral particles).

Concentration may comprise any suitable methods known in the art that concentration of lentiviral vector particles in the composition (typically measured as an infectious titer of lentiviral particles and/or a physical titer of lentiviral particles).

At least one purification step is typically (although not always) performed before the first concentration step. In some embodiments purification and concentration occurs simultaneously. Examples of methods that may be used for purification and concentration are ion exchange chromatography and ultrafiltration.

In some embodiments of the methods the purifying and concentrating occurs in the absence of polyethylene glycol. In some embodiments of the methods the purifying and concentrating occurs in the presence of no more than 0.1 M polyethylene glycol.

In some embodiments, the concentrated and purified lentiviral vector particles following purification and concentration lentiviral vector particles are present at a concentration of at least $1\times10^6$ TU/mL, at least $2\times10^6$ TU/mL, at least $3\times10^6$ TU/mL, at least $4\times10^6$ TU/mL, at least $5\times10^6$ TU/mL, at least $6\times10^6$ TU/mL, at least $7\times10^6$ TU/mL, at least $8\times10^6$ TU/mL, at least $9\times10^6$ TU/mL, at least $1\times10^7$ TU/mL, at least $2\times10^7$ TU/mL, at least $3\times10^7$ TU/mL, at least $4\times10^7$ TU/mL, at least $5\times10^7$ TU/mL, at least $6\times10^7$ TU/mL, at least $7\times10^7$ TU/mL, at least $8\times10^7$ TU/mL, at least $9\times10^7$ TU/mL, at least $1\times10^8$ TU/mL, at least $2\times10^8$ TU/mL, at least $3\times10^8$ TU/mL, at least $4\times10^8$ TU/mL, at least $5\times10^8$ TU/mL, at least $6\times10^8$ TU/mL, at least $7\times10^8$ TU/mL, at least $8\times10^8$ TU/mL, at least $9\times10^8$ TU/mL, or at least $1\times10^9$ TU/mL.

In some embodiments, the concentrated and purified lentiviral vector particles are present at a concentration of from $1\times10^5$ TU/mL to $1\times10^9$ TU/mL, from $1\times10^6$ TU/mL to $1\times10^9$ TU/mL, from $1\times10^7$ TU/mL to $1\times10^9$ TU/mL, from $1\times10^8$ TU/mL to $1\times10^9$ TU/mL, from $1\times10^5$ TU/mL to $1\times10^7$ TU/mL, from $1\times10^6$ to $1\times10^8$ TU/mL, from $1\times10^7$ to $1\times10^9$ TU/mL, from $5\times10^7$ TU/mL to $1\times10^8$ TU/mL, from $1\times10^8$ TU/mL to $5\times10^8$ TU/mL, or from $5\times10^8$ TU/mL to $1\times10^9$ TU/mL.

In some embodiments, the concentrated and purified lentiviral vector particles comprise no more than 20,000 ng, no more than 15,000 ng, no more than 10,000 ng, no more than 8,000 ng, no more than 6,000 ng, no more than 4,000 ng, no more than 2,000 ng, or no more than 1,000 ng of total DNA per $1\times10^7$ TU, per $5\times10^7$ TU, per $1\times10^8$ TU, per $5\times10^8$ TU, or per $1\times10^9$ TU. In some embodiments following purification and concentration the concentrated lentiviral vector particles produced in c) comprise from 1,000 ng to 20,000 ng, from 1,000 ng to 15,000 ng, from 1,000 ng to 10,000 ng, from 1,000 ng to 5,000 ng, or from 1,000 ng to 4,000 ng of total DNA per $1\times10^7$ TU, per $5\times10^7$ TU, per $1\times10^8$ TU, per $5\times10^8$ TU, or per $1\times10^9$ TU.

In some embodiments, the concentrated and purified lentiviral vector particles comprise no more than 5,000 μg, no more than 4,000 μg, no more than 3,000 μg, no more than 2,000 μg, no more than 1,600 μg, no more than 1,200 μg, no more than 800 μg, no more than 400 μg, or no more than 200 μg of total protein per $1\times10^7$ TU, per $5\times10^7$ TU, per $1\times10^8$ TU, per $5\times10^8$ TU, or per $1\times10^9$ TU. In some embodiments following purification and concentration the concentrated lentiviral vector particles produced in c) comprise from 200 μg to 5,000 μg, from 200 μg to 4,000 μg, from 200 μg to 3,000 μg, from 200 μg to 2,000 μg, from 200 μg to 1,000 μg, from 500 up to 1,000 μg, from 1,000 μg to 1,500 μg, from 1,500 μg to 2,000 μg, from 2,000 μg to 2,500 μg, from 2,500 μg to 3,000 μg, from 3,500 μg to 4,000 μg, from 4,000 to 4,500 μg, or from 4,500 μg to 5,000 μg of total protein per $1\times10^7$ TU, per $5\times10^7$ TU, per $1\times10^8$ TU, per $5\times10^8$ TU, or per $1\times10^9$ TU.

In some embodiments, the concentrated and purified lentiviral vector particles comprise no more than 8,000 ng, no more than 7,000 ng, no more than 6,000 ng, no more than 5,000 ng, no more than 4,000 ng, no more than 3,000 ng, no more than 2,000 ng, no more than 1,000 ng, or no more than 500 ng of host cell protein per $1\times10^7$ TU, per $5\times10^7$ TU, per $1\times10^8$ TU, per $5\times10^8$ TU, or per $1\times10^9$ TU. In some embodiments following purification and concentration the concentrated lentiviral vector particles produced in c) comprise from 500 ng to 8,000 ng, from 1,000 ng to 6,000 ng, from 2,000 ng to 4,000 ng, from 3,000 ng to 5,000 ng, or from 4,000 ng to 6,000 ng of total DNA per $1\times10^7$ TU, per $5\times10^7$ TU, per $1\times10^8$ TU, per $5\times10^8$ TU, or per $1\times10^9$ TU.

In some embodiments, the concentrated and purified lentiviral vector particles comprise no more than 30,000 ng, no more than 25,000 ng, no more than 20,000 ng, no more than 15,000 ng, no more than 10,000 ng, or no more than 5,000 ng, of serum albumin per $1\times10^7$ TU, per $5\times10^7$ TU, per $1\times10^8$ TU, per $5\times10^8$ TU, or per $1\times10^9$ TU. In some embodiments following purification and concentration the concentrated lentiviral vector particles produced in c) comprise from 5,000 ng to 30,000 ng, from 10,000 ng to 25,000 ng, from 10,000 ng to 20,000 ng, from 15,000 ng to 30,000 ng, or from 20,000 ng to 35,000 ng of serum albumin per $1\times10^7$ TU, per $5\times10^7$ TU, per $1\times10^8$ TU, per $5\times10^8$ TU, or per $1\times10^9$ TU.

In some embodiments, the concentrated and purified lentiviral vector particles comprise an infectious titer of at least $1\times10^6$ TU, at least $5\times10^6$ TU $1\times10^7$ TU, at least $5\times10^7$ TU, at least $1\times10^8$ TU, at least $5\times10^8$ TU, or at least $1\times10^9$ TU.

In some embodiments, the concentrated and purified lentiviral vector particles comprise no more than 1, 2, 5, 10, 20, or 50 ng of non-human serum albumin/ml. In some embodiments, the concentrated and purified lentiviral vector particles comprise no more than 1, 2, 5, 10, 20, or 50 ng of serum albumin (total, human or non-human)/$10^8$ or/$10^7$ TU.

In some embodiments the concentrated and purified lentiviral vector particles are frozen and/or lyophilized in the presence of no more than 1.0%, 0.5%, 0.2%, 0.1% 0.05%, 0.02%, 0.01%, or no serum albumin (total, human or non-human).

In some embodiments the purifing in b) comprises clarifying the cell supernatant of a), and the amount of total DNA per TU present in the concentrated lentiviral vector particles produced in c) is no more than 40%, no more than 35%, no more than 30%, no more than 25%, or no more than 20% of the amount of total DNA per TU present in the cell supernatant.

In some embodiments the purifing in b) comprises clarifying the cell supernatant of a), and wherein the amount of total protein per TU present in the concentrated lentiviral vector particles produced in c) is no more than 2.0%, no more than 1.5%, no more than 1.0%, or no more than 0.5% of the amount of total DNA per TU present in the cell supernatant.

In some embodiments the purifing in b) comprises clarifying the cell supernatant of a), and wherein the amount of host cell proteins per TU present in the concentrated lentiviral vector particles produced in c) is no more than 2.0%, no more than 1.5%, no more than 1.0%, or no more than 0.5% of the amount of total DNA per TU present in the cell supernatant.

In some embodiments the purifing in b) comprises clarifying the cell supernatant of a), and wherein the amount of serum albumin per TU present in the concentrated lentiviral vector particles produced in c) is no more than 0.20%, no more than 0.15%, no more than 0.10%, or no more than 0.05% of the amount of total DNA per TU present in the cell supernatant.

In some embodiments at least one lyoprotectant is used. In some embodiments the total concentration of lyoprotectant present in d) is from 0.1 M to 2 M, from 0.2 M to 1.5 M, from 0.5 M to 1 M, from 1M to 1.5 M, or from 0.5 M to 1.5 M. In some embodiments two or more different lyoprotectants are present.

In some embodiments the lyophilized lentiviral vector particles are stored for at least 1 day, at least 2 days, at least 3 days, at least 4 days, at least 5 days, at least 6 days, at least 7 days, at least 15 days, at least 30 days, at least 45 days, at least 60 days, or at least 70 days. In some embodiments the lyophilized lentiviral vector particles are stored for from 1 to 3 days, from 1 to 7 days, from 1 to 15 days, from 1 to 30 days, from 1 to 45 days, from 1 to 60 days, or from 1 to 70 days. In some embodiments the lyophilized lentiviral vector particles are stored for from 3 to 7 days, from 3 to 15 days, from 7 to 15 days, from 7 to 30 days, from 115 to 45 days, from 30 to 60 days, or from 15 to 70 days.

In some embodiments the lyophilized lentiviral vector particles are stored at from −80° C. to 20° C., from −80° C. to −20° C., from −20° C. to 4° C., from 4° C. to 20° C., from −1° C. to 9° C., from −25° C. to −15° C., or from 15° to 25° C.

In some embodiments the lentiviral particle titer after storing is at least 40% at least 50%, at least 60%, at least 70%, at least 75%, at least 80%, at least 85%, at least 90%, or at least 95% of the lentiviral particle titer after freezing and before lyophilizing. In some embodiments the lentiviral particle titer after storing is from 50 to 95%, from 50 to 60%, from 60 to 70%, from 70 to 80%, from 80 to 90%, or from 80 to 95% of the lentiviral particle titer after freezing and before lyophilizing.

Compositions Comprising Lyophilized Lentiviral Particles

The invention also encompasses compositions comprising lyophilized lentiviral particles. In some embodients, when the lentiviral particles are reconstituted in the freeze volume the lentiviral vector particles are present in the composition at a concentration of at least $1\times10^6$ TU/mL, at least $2\times10^6$ TU/mL, at least $3\times10^6$ TU/mL, at least $4\times10^6$ TU/mL, at least $5\times10^6$ TU/mL, at least $6\times10^6$ TU/mL, at least $7\times10^6$ TU/mL, at least $8\times10^6$ TU/mL, at least $9\times10^6$ TU/mL, at least $1\times10^7$ TU/mL, at least $2\times10^7$ TU/mL, at least $3\times10^7$ TU/mL, at least $4\times10^7$ TU/mL, at least $5\times10^7$ TU/mL, at least $6\times10^7$ TU/mL, at least $7\times10^7$ TU/mL, at least $8\times10^7$ TU/mL, at least $9\times10^7$ TU/mL, at least $1\times10^8$ TU/mL, at least $2\times10^8$ TU/mL, at least $3\times10^8$ TU/mL, at least $4\times10^8$ TU/mL, at least $5\times10^8$ TU/mL, at least $6\times10^8$ TU/mL, at least $7\times10^8$ TU/mL, at least $8\times10^8$ TU/mL, at least $9\times10^8$ TU/mL, or at least $1\times10^9$ TU/mL.

In some embodiments, when the lentiviral particles are reconstituted in the freeze volume the lentiviral vector particles are present in the composition at a concentration of from $1\times10^5$ TU/mL to $1\times10^9$ TU/mL, from $1\times10^6$ TU/mL to $1\times10^9$ TU/mL, from $1\times10^7$ TU/mL to $1\times10^9$ TU/mL, from $1\times10^8$ TU/mL to $1\times10^9$ TU/mL, from $1\times10^5$ TU/mL to $1\times10^7$ TU/mL, from $1\times10^6$ to $1\times10^8$ TU/mL, from $1\times10^7$ to $1\times10^9$ TU/mL. In some embodiments the composition comprises no more than 20,000 ng, no more than 15,000 ng, no more than 10,000 ng, no more than 8,000 ng, no more than 6,000 ng, no more than 4,000 ng, no more than 2,000 ng, or no more than 1,000 ng of total DNA per $1\times10^7$ TU, per $5\times10^7$ TU, per $1\times10^8$ TU, per $5\times10^8$ TU, or per $1\times10^9$ TU. In some embodiments the composition comprises from 1,000 ng to 20,000 ng, from 1,000 ng to 15,000 ng, from 1,000 ng to 10,000 ng, from 1,000 ng to 5,000 ng, or from 1,000 ng to 4,000 ng of total DNA per $1\times10^7$ TU, per $5\times10^7$ TU, per $1\times10^8$ TU, per $5\times10^8$ TU, or per $1\times10^9$ TU.

In some embodiments the composition comprises no more than 5,000 μg, no more than 4,000 μg, no more than 3,000 μg, no more than 2,000 μg, no more than 1,600 μg, no more than 1,200 μg, no more than 800 μg, no more than 400 μg, or no more than 200 μg of total protein per $1\times10^7$ TU, per $5\times10^7$ TU, per $1\times10^8$ TU, per $5\times10^8$ TU, or per $1\times10^9$ TU. In some embodiments the composition comprises from 200 μg to 5,000 μg, from 200 μg to 4,000 μg, from 200 μg to 3,000 μg, from 200 μg to 2,000 μg, from 200 μg to 1,000 μg, from 500 up to 1,000 μg, from 1,000 μg to 1,500 μg, from 1,500 μg to 2,000 μg, from 2,000 μg to 2,500 μg, from 2,500 μg to 3,000 μg, from 3,500 μg to 4,000 μg, from 4,000 to 4,500 μg, or from 4,500 μg to 5,000 μg of total protein per $1\times10^7$ TU, per $5\times10^7$ TU, per $1\times10^8$ TU, per $5\times10^8$ TU, or per $1\times10^9$ TU.

In some embodiments the composition comprises no more than 8,000 ng, no more than 7,000 ng, no more than 6,000 ng, no more than 5,000 ng, no more than 4,000 ng, no more than 3,000 ng, no more than 2,000 ng, no more than 1,000 ng, or no more than 500 ng of host cell protein per $1\times10^7$ TU, per $5\times10^7$ TU, per $1\times10^8$ TU, per $5\times10^8$ TU, or per $1\times10^9$ TU. In some embodiments the composition comprises from 500 ng to 8,000 ng, from 1,000 ng to 6,000 ng, from 2,000 ng to 4,000 ng, from 3,000 ng to 5,000 ng, or from 4,000 ng to 6,000 ng of total DNA per $1\times10^7$ TU, per $5\times10^7$ TU, per $1\times10^8$ TU, per $5\times10^8$ TU, or per $1\times10^9$ TU.

In some embodiments the composition comprises no more than 30,000 ng, no more than 25,000 ng, no more than 20,000 ng, no more than 15,000 ng, no more than 10,000 ng, or no more than 5,000 ng, of serum albumin (total, human or non-human) per $1\times10^7$ TU, per $5\times10^7$ TU, per $1\times10^8$ TU, per $5\times10^8$ TU, or per $1\times10^9$ TU. In some embodiments the composition comprises from 5,000 ng to 30,000 ng, from 10,000 ng to 25,000 ng, from 10,000 ng to 20,000 ng, from 15,000 ng to 30,000 ng, or from 20,000 ng to 35,000 ng of serum albumin per $1\times10^7$ TU, per $5\times10^7$ TU, per $1\times10^8$ TU, per $5\times10^8$ TU, or per $1\times10^9$ TU.

In some embodiments the lyophilized composition comprising lentiviral vector particles comprises no more than 1.0%, 0.5%, 0.2%, 0.1% 0.05%, 0.02%, 0.01%, or no serum albumin (total, human or non-human).

In some embodiments the composition comprises at least one lyoprotectant. In some embodiments the total concentration of lyoprotectant present in the composition is from 0.1 M to 2 M, from 0.2 M to 1.5 M, from 0.5 M to 1 M, from 1M to 1.5 M, or from 0.5 M to 1.5 M. In some embodiments two or more different lyoprotectancts are present.

In some embodiments the lyophilized composition comprising lentiviral vector particles has been stored lyophilized for at least 1 day, at least 2 days, at least 3 days, at least 4 days, at least 5 days, at least 6 days, at least 7 days, at least 15 days, at least 30 days, at least 45 days, at least 60 days, or at least 70 days. In some embodiments the lyophilized composition comprising lentiviral vector particles has been stored lyophilized for from 1 to 3 days, from 1 to 7 days, from 1 to 15 days, from 1 to 30 days, from 1 to 45 days, from 1 to 60 days, or from 1 to 70 days. In some embodiments the lyophilized composition comprising lentiviral vector particles has been stored lyophilized for from 3 to 7 days, from 3 to 15 days, from 7 to 15 days, from 7 to 30 days, from 115 to 45 days, from 30 to 60 days, or from 15 to 70 days.

In some embodiments the lyophilized composition comprising lentiviral vector particles have been stored lyophilized for at from −1° C. to 9° C., from −25° C. to −15° C., or from 15° to 25° C.

The invention encompasses lyophilized lentiviral vector particles for use as a pharmaceutical composition, a vaccine, or an immunogenic composition in a human subject. The invention also encompasses lyophilized lentiviral vector particles for use as a pharmaceutical composition, a vaccine, or an immunogenic composition in a human subject Methods of Administration The invention encompasses methods of administration of a lentiviral vector particle to a human subject and uses of the lyophilized lentiviral vector particles for administration to human subjects as a vaccine or therapy.

The present invention further relates to the use of the lyophilized lentiviral vector particles for the preparation of therapeutic compositions or vaccines which are capable of inducing or contributing to the occurrence or improvement of an immunological reaction.

In some embodiments the lentiviral vector particle contains a promoter that drives high expression of a protein in at least one cell type of the subject. In some embodiments the protein is an antigen. In some embodiments expression is driven in antigen presenting cells, including dendritic cells, and drives expression in other transduced cell types sufficient for elimination by the induced immune response. In some embodiments the lentivector particle is an integrating lentivector particle, comprising a functional integrase protein.

In some embodiments, the lentiviral vector particles are in a dose of $1\times10^6$ TU, $2\times10^6$ TU, $3\times10^6$ TU, $4\times10^6$ TU, $5\times10^6$ TU, $6\times10^6$ TU, $7\times10^6$ TU, $8\times10^6$ TU, $9\times10^6$, $1\times10^7$ TU, $2\times10^7$ TU, $3\times10^7$ TU, $4\times10^7$ TU, $5\times10^7$ TU, $6\times10^7$ TU, $7'10^7$ TU, $8\times10^7$ TU, $9\times10^7$ TU, $1\times10^8$ TU, $2\times10^8$ TU, $3\times10^8$ TU, $4\times10^8$ TU, $5\times10^8$ TU, $6\times10^8$ TU, $7\times10^8$ TU, $8\times10^8$ TU, $9\times10^8$ TU, or $1\times10^9$ TU. In some embodiments, the lentiviral vector particles are in a dose of from $1\times10^6$ TU to $5\times10^6$ TU, from $5\times10^6$ TU to $1\times10^7$ TU, from $1\times10^7$ TU to $5\times10^7$ TU, from $5\times10^7$ TU to $1\times10^8$ TU, from $1\times10^8$ TU to $5\times10^8$ TU, or from $5\times10^8$ TU to $1\times10^9$ TU.

Preferably, the dose of lentiviral particles is a solution of resuspended lyophilized lentiviral particles. In one embodiment, the method comprises administering a dose of resuspended lyophilized lentiviral particles to a human subject, preferably intramuscularly.

In one embodiment, the method comprises resuspending a dose of lyophilized lentiviral particles in an aqueous, sterile solution and administering it to a human subject, preferably intramuscularly.

The immune response induced by the lentiviral vector can be a B cell response, a CD4+ T cell response, and/or a CD8+ T cell response.

In some embodiments the lentiviral vector particles are provided in the form of a lyophilized composition. In some embodiments the lyophilized composition is made by a method of this invention. In some embodiments the lyophilized composition is a lyophilized composition according to this invention. Typically the lyophilized composition is reconstituted in a pharmaceutically acceptable solution for administration to the subject.

EXAMPLES

Aspects of the present teachings can be further understood in light of the following examples, which should not be construed as limiting the scope of the present teachings in any way.

Example 1

Lentiviral Vector Particle Production

For preclinical and GMP productions, the lentiviral vectors THV01-1 (β2m-HIV pseudotyped with Indiana VSV-G), THV01-2 (β2m-HIV pseudotyped with New Jersey VSV-G) and THV01-3 (β2m-HIV pseudotyped with Cocal) carried the same antigen, but they were pseudotyped with different envelope isoforms. Regarding R&D productions, the lentiviral vector carried the EGFP protein as antigen and it was pseudotyped with Indiana VSV-G.

R&D productions: Vectors were produced by transient calcium-phosphate transfection of HEK 293T as previously describe (Zennou, V. et al. HIV-1 genome nuclear import is mediated by a central DNA flap. *Cell.* 101, 173-185 (2000).

Preclinical and GMP productions: The day before transfection, HEK 293T cells were seeded in culture medium on 24 units of Cell Factory 10 (CF-10, Nunc). Cells were transfected by a calcium-phosphate method as reported previously (25). 18 to 24 hours post-transfection, culture medium was changed with production medium corresponding to Dulbecco's modified Eagle's medium (DMEM/High modified, Hyclone) supplemented with 2% heat-inactivated fetal calf serum (FCS, PAA), 1% L-Glutamine (Gibco by Life technologies), 1% Penicillin-Streptomycin (Gibco by Life technologies), 1% Sodium Pyruvate (Gibco by Life technologies), BENZONASE® (pharma grade I, 100 000U, Merck Millipore) and MgCL2 1M. Minimum 24 hours after medium renewal, supernatant of the 24 CF-10 was harvested and pooled. After a second BENZONASE® treatment, supernatant was clarified by filtration on Kleenpak Nova Profile II cartridge (Pall). After clarification, a third BENZONASE® treatment was applied overnight at +2/+8° C. Viral vector were purified using Anion exchange chromatography on Mustang-Q XT cassette (Pall). Lentiviral particles were eluted in two steps with 0.5M and 1.2M NaCl. Both fractions were diluted to decrease NaCl concentration up to ±150 mM before pooling. IEX eluate was further concentrated approximately 40 fold by ultrafiltration using a 100 KDa Omega T series filter, 0.1 $m^2$ (Pall) and diafiltrated with PBS-Lactose 40 mg.L-1. Purified bulk (Drug substance) was finally filtered through a 0.2 μM Sartobran H5 filter, 300 $cm^2$ (Sartorius Stedim) and aseptically distributed on 2R 3 mL-glass vials with a target filling volume of 650 μL (1200 μL for pilot batches). After visual inspection of all the vials (about 350 vials by clinical batch), drug product was stored at −70° C.±10° C.

For product characterization and pharmaceutical release, quality tests were performed according to regulatory texts on vaccines: the quality control required for vaccines as per the European Pharmacopeia (section 6.16), the "guideline on quality, non-clinical and clinical aspects of live recombinant viral vectored vaccines" (EMA/CHMP/141697/2009), the "guideline on development and manufacture of lentiviral vectors" (CHMP/BWP/2458/03); regulatory text on gene therapy medicinal products: the quality controls required for gene transfer medicinal products for human use as per the European Pharmacopeia (section 5.14), the quality controls specific to gene therapy products as defined in the "note for guidance on the quality, preclinical and clinical aspects of gene transfert medicinal products" (CHMP/BWP/3088/99); regulatory texts on biotechnological products (ICH Q5A to ICH Q5E); regulatory texts on specifications (ICH Q6A and ICH Q6B) and the quality controls required for parenteral preparations as per the European Pharmacopeia (section 7.0).

Example 2

Lentiviral Vector Particle Titration

Number of total physical particles (effective plus deficient) was assessed by a commercial ELISA kit for quantification of the P24 protein in solution (#NEK050B, Perkin Elmer). The method is based on a sandwich ELISA and is performed according to manufacturer instructions. This value is reported in the Tables below as the "physical titer" for preclinical and GMP productions. For preclinical and GMP productions, infectious titers were determined by qPCR (quantification of the lentiviral integrated proviral DNA in host cell genome) and for R& D productions, infectious titers were determined by flow cytometry based on EGFP expression.

qPCR reactions: HEK 293T cells were seeded in 6-well plates (BD Falcon) in culture medium and incubated for 4 h at 37° C., 5% CO2 in moist atmosphere. Cells were transduced with 3 successive dilutions of lentiviral vector. 72 h post-incubation, cells are harvested and transduced HEK 293T cell pellets are produced. Total genomic DNA from transduced cell-pellets is extracted using a method based on QIAGEN QIAamp DNA mini kit handbook. Proviral quantification is performed using Taqman qPCR. The amplification is performed with the Master Mix (Fermentas Thermo Scientific), the Flap A (CCCAAGAACCCAAGGAACA;) and Flap S (AGACAA GATAGAGGAAGAGCAAAAC) primers and LENTI™ probe (6FAM-AACCATTAGGAGTAGCACCCACCAAGG-BBQ). Normalization is performed with the quantification of the actin gene (same Mix, Actine A—CGGTGAGGATCTTCATGAGGTAGT), Actine S—AACACCCCAGCCATGTACGTprimers and HUMURA ACT™ probe-6FAM-CCAGCCAGGTCCAGACGCAGGA-BBQ. Both reactions are achieved on MasterCycler Ep Realplex S (Eppendorf, 2 min at 50° C., 10 min at 95° C. and 40 cycles of 15 seconds at 95° C. and 1 min at 63° C.). The analysis is performed on MasterCycler Ep Realplex Software.

FACS analyses were performed as described elsewhere (Beignon, A. S., et al. Lentiviral vector-based prime/boost vaccination against AIDS: pilot study shows protection against Simian immunodeficiency virus SIVmac251 challenge in macaques. *J Virol.* 83, 10963-10974 (2009).

Animals: For non-GLP studies, C57BL/6J Rj (C57Bl/6J) female mice of four weeks or Sprague Dawley RjHan:SD (Sprague Dawley) female mice of eight weeks were purchased from Janvier Laboratories (France). The animals were housed in Institute Pasteur animal facility in accordance with Institute regulations on the respect of animal experimentation ethical procedures. For GLP studies males and females of CRL: CD strain of rats were purchased from Charles River Italia, Calco (LC), Italy (aged of at least 10 weeks). Rats were housed in our CRO (APTUIT) facilities.

Sample collection and cell isolation: after CO2 euthanasia, rats' spleens were perfused and chopped into small pieces before being gently squished on a 100 μm cell stainer whilst mice spleens were directly squished on the cell stainer. Red Blood Cell Lysing Buffer Hybri-Max (Sigma Aldrich) was used to lyse red blood cells. Following three further washes splenocytes were resuspended into RPMI1640 medium containing 10% FBS and automatically counted using Nucleocounter Chemometec cells counter.

Example 3

Analysis of Purified and Concentrated Lentiviral Vector Particles

The lentiviral vector particles were analyzed at several steps of the production process described in Example 1.

Physical titer was determined as described in Example 2.

Infectious titer was determined as described in Example 2.

Total residual DNA was measured with the Quant-iT™ PicoGreen® dsDNA (Invitrogen Ref #P7589) as described by the manufacturer. The Quant-iT™ PicoGreen® dsDNA reagent is a fluorescent nucleic acid stain. This kit is able to quantitate dsDNA with a spectrofluorometer and fluorescein excitation and emission wavelengths. The Quant-iT™ PicoGreen® minimizes the fluorescence contribution of RNA and single-stranded DNA. The spectrofluorometer used for R&D lentiviral vector is the TriStar$^2$ LB 942 Multidetection Microplate Reader (Berthold Technologies) with the following features: emission 485 nm, emission 535 nm, lamp energy: 8%, counting time 0.10 seconds.

Total protein was measured with Bicinchoninic Acid (BCA) Protein Assay kit (Sigma-Aldrich Ref #BCA1-1KT) as follows. The working solution of BCA was prepared by mixing 50 volumes of reagent A with 1 volume of reagent B. The working solution is then added to sample in a ratio 1:1. The solution is incubated 30 min à 37° C. The measure is then directly carried-out with a Nanodrop 2000c. The Nanodrop measures the absorbance of the purple-blue complex at 562 nm. The BCA assay is based on the formation of a $Cu^{2+}$-protein complex under alkaline conditions, followed by reduction of $Cu^{2+}$ to $Cu^{1+}$. The reduction is due to the presence of amino acid (e.g: cysteine, tryptophan, tyrosine). The reduction is visible with appearance of a purple-blue complex formed by the BCA in alkaline environments. In consequence, the amount of reduction is proportional to the protein concentration.

HEK 293 Host Cell Proteins was measured with the HEK 293 Host Cell Proteins 2$^{nd}$ Generation (Cygnus Technologies Ref #F650) as described by the manufacturer. The kit, based on the ELISA assay, is intended for the determination of the impurities derived from HEK 293 cell line present in products manufactured with HEK 293 T cell lines. The Cygnus kit is a two-site immunoenzymetric assay. Samples' impurities are reacted with affinity purified antibodies coated on a microtiter strip and with Horseradish peroxidase (HRP) labeled anti-HRP antibodies (goat polyclonal). The TMB (substrate of the HRP) is hydrolyzed and gives a colorimetric quantification of the amount of HRP which is directly proportional to the amount of HEK 293 proteins. The spectrofluorometer used for R&D lentiviral vector is the TriStar$^2$LB 942 Multidetection Microplate Reader (Berthold Technologies) with the following feature: absorbance 450 nm.

Residual benzonase was quantified on preclinical and GMP production by a commercial ELISA kit (ref #1.01681.0001, Merck).

Residual BSA from cell culture was measured using ELISA assays (Cygnus Technologies Ref #F030) as described by the manufacturer. The kit, based on the ELISA assay, is intended for the determination of the amount of BSA derived from cell culture process. The Cygnus kit is a two-site immunoenzymetric assay. BSA containing in samples are reacted with affinity purified antibodies coated on a microtiter strip and with Horseradish peroxidase (HRP) labeled anti-HRP antibodies. The TMB (substrate of the HRP) is hydrolyzed and gives a colorimetric quantification of the amount of HRP which is directly proportional to the amount of BSA. The spectrofluorometer used for R&D lentiviral vector is the TriStar$^2$ LB 942 Multidetection Microplate Reader (Berthold Technologies) with the following feature: absorbance 450 nm.

The results of the analysis of the preclinical and GMP productions are provided in Table 1A. The results of the analysis of the R&D productions are presented in Table 1B.

The effective yields of lentiviral vector particles in the preclinical and GMP productions relative to the harvested bulk material collected directly from the culture medium (see Table 1A) is presented in Table 2. The mean retention yield is calculated as a percentage of the harvested bulk yield.

Table 3 presents the mean retention yield of the measured contaminants in the preclinical and GMP productions (see Table 1A). Here the mean retention yield is calculated relative to the yield at the clarified harvest stage.

TABLE 1A

| FRACTION | QUALITY CONTROL | UNITS | MEAN RESULT (N = 5) |
|---|---|---|---|
| Clarified Harvest | Physical Titer, ELISA p24 | ng/mL | 1270.7 ± 761.9 |
| | Infectious Titer, TaqMan qPCR | TU/mL | 3.64 ± 1.43E+07* |
| | Total residual DNA, Picogreen | ng/mL | 347.0 ± 244.4 |
| | Total protein, μBCA | μg/mL | 2744.7 ± 432.7* |
| | HEK 293T Host Cell Protein, ELISA | ng/mL | 8037.7 ± 6805.7 |
| | Residual Benzonase, ELISA | ng/mL | 4.7 ± 0.7* |
| | Residual BSA, ELISA | ng/mL | 398956.7 ± 88419.2* |
| Drug Substance | Physical Titer, ELISA p24 | ng/mL | 187011.3 ± 209700.2 |
| | Infectious Titer, TaqMan qPCR | TU/mL | 8.31 ± 8.29E+08* |
| | Total residual DNA, Picogreen | ng/mL | 4518.0 ± 3322.9 |
| | Total protein, μBCA | μg/mL | 1521.0 ± 445.0 |
| | HEK 293T Host Cell Protein, ELISA | ng/mL | 4054.9 ± 3430 |
| | Residual Benzonase, ELISA | ng/mL | 0.2 ± 0.0 |
| | Residual BSA, ELISA | ng/mL | 15984.6 ± 3329.9 |
| | Endotoxins | IU/mL | 2.2 ± 2.1 |
| | Bioburden | CFU/mL | 0.0 ± 0.0 |
| Drug Product | Physical Titer, ELISA p24 | ng/mL | 201874.9 ± 329151.2 |
| | Infectious Titer, TaqMan qPCR | TU/mL | 2.92 ± 1.30E+08 |
| | Total residual DNA, Picogreen | ng/mL | 2167.6 ± 630.4 |
| | Total protein, μBCA | μg/mL | 1399.9 ± 442.6 |
| | HEK 293T Host Cell Protein, ELISA | ng/mL | 2815.8 ± 2269.9* |
| | Residual Benzonase, ELISA | ng/mL | 0.2 ± 0.0* |
| | Residual BSA, ELISA | ng/mL | 14272.3 ± 4156.6* |
| | Endotoxins | IU/mL | 1.6 ± 1.5 |

*n = 3, mean calculated only on preclinical batches

TABLE 1B

| Fraction | Quality Control | Units | Mean Result |
|---|---|---|---|
| Clarified Harvest (n = 7) | Total residual DNA, Picogreen | ng/mL | 681.3 ± 337.7 |
| | Total protein, BCA | μg/mL | 1199.3 ± 386.9 |
| | HEK 293T Host Cell Protein, ELISA | ng/mL | 6113.5 ± 4568.1 |
| | Residual BSA, ELISA | ng/mL | 127965.1 ± 126838.7 |
| Drug Substance (n = 4) | Total residual DNA, Picogreen | ng/mL | 7962.2 ± 6527.3 |
| | Total protein, BCA | μg/mL | 363.3 ± 390.1 |
| | HEK 293T Host Cell Protein, ELISA | ng/mL | 3080.3 ± 1329.9 |
| | Residual BSA, ELISA | ng/mL | 14093.0 ± 12371.6 |

TABLE 2

| FRACTION | QUALITY CONTROL | MEAN RETENTION YIELD % (N = 5) |
|---|---|---|
| Harvest Bulk | Physical Titer, ELISA p24 | 100.00 ± 0.00 |
| | Infectious Titer, TaqMan qPCR | 100.00 ± 0.00* |
| Clarified Harvest | Physical Titer, ELISA p24 | 93.24 ± 19.14 |
| | Infectious Titer, TaqMan qPCR | 72.94 ± 6.40* |
| Drug Substance | Physical Titer, ELISA p24 | 123.84 ± 74.60 |
| | Infectious Titer, TaqMan qPCR | 17.27 ± 14.05* |
| Drug Product | Physical Titer, ELISA p24 | 126.25 ± 145.01 |
| | Infectious Titer, TaqMan qPCR | 6.32 ± 2.21* |

*n = 3, mean calculated only on preclinical batches

TABLE 3

| FRACTION | QUALITY CONTROL | MEAN RETENTION YIELD % (N = 5) |
|---|---|---|
| Clarified Harvest | Total residual DNA, Picogreen | 100.00 ± 0.00 |
| | Total protein, μBCA | 100.00 ± 0.00* |
| | HEK 293T Host Cell Protein, ELISA | 100.00 ± 0.00 |
| | Residual Benzonase, ELISA | 100.00 ± 0.00* |
| | Residual BSA, ELISA | 100.00 ± 0.00* |
| Drug Substance | Total residual DNA, Picogreen | 20.23 ± 15.50 |
| | Total protein, μBCA | 0.71 ± 0.12* |
| | HEK 293T Host Cell Protein, ELISA | 0.61 ± 0.41 |
| | Residual Benzonase, ELISA | 0.38 ± 0.66 |
| | Residual BSA, ELISA | 0.04 ± 0.00* |
| Drug Product | Total residual DNA, Picogreen | 10.46 ± 7.68 |
| | Total protein, μBCA | 0.65 ± 0.15* |
| | HEK 293T Host Cell Protein, ELISA | 0.55 ± 0.27* |
| | Residual Benzonase, ELISA | 0.05 ± 0.01* |
| | Residual BSA, ELISA | 0.04 ± 0.00* |

*n = 3, mean calculated only on preclinical batches

The data presented in Tables 1A and 3 show that the residual DNA is reduced by an average of over 79%, the amount of total protein by an average of over 99%, the amount of host cell protein by an average of over 99%, and the amount of BSA by an average of over 99.9%.

As shown in Table 1, these methods enable production of lentiviral compositions comprising over $1\times10^8$ TU/ml of lentiviral particles and comprising less than 1400 μg/mL total protein, less than 2816 ng/mL host cell protein, less than 2168 ng/mL residual DNA, and less than 14273 ng/mL residual BSA.

Example 4

Stability of Frozen Lentiviral Vector Particles

Lentiviral vector particle suspensions produced as in Example 1 (preclinical and GMP productions) were diluted in PBS or Tris+/−sugars (Trehalose 0.5 M/Sucrose 0.5 M) and frozen at −80° C. The suspensions were thawed and viral titers were determined at various time points. The lentiviral particles used in this example were processed to the Drug Substance stage.

In a first experiment lentiviral particles suspended in PBS buffer (PBS/Lactose 40 mg/L), PBS buffer plus 0.5 M sucrose, PBS buffer plus 0.5 M trehalose, Tris buffer (20 mM Tris pH 7.5/$MgCl_2$ 2 mM/Lactose 40 mg/L), Tris buffer plus 0.5 M sucrose, or Tris buffer plus 0.5 M trehalose and then frozen at 80° C. for 24 hrs. The particles were then thawed and the infectious titer was measured. As shown in FIGS. 1A (PBS buffered solutions) and 1B (Tris buffered solutions) there was no significant difference in lentiviral vector stability between the two buffers.

Figure 2:
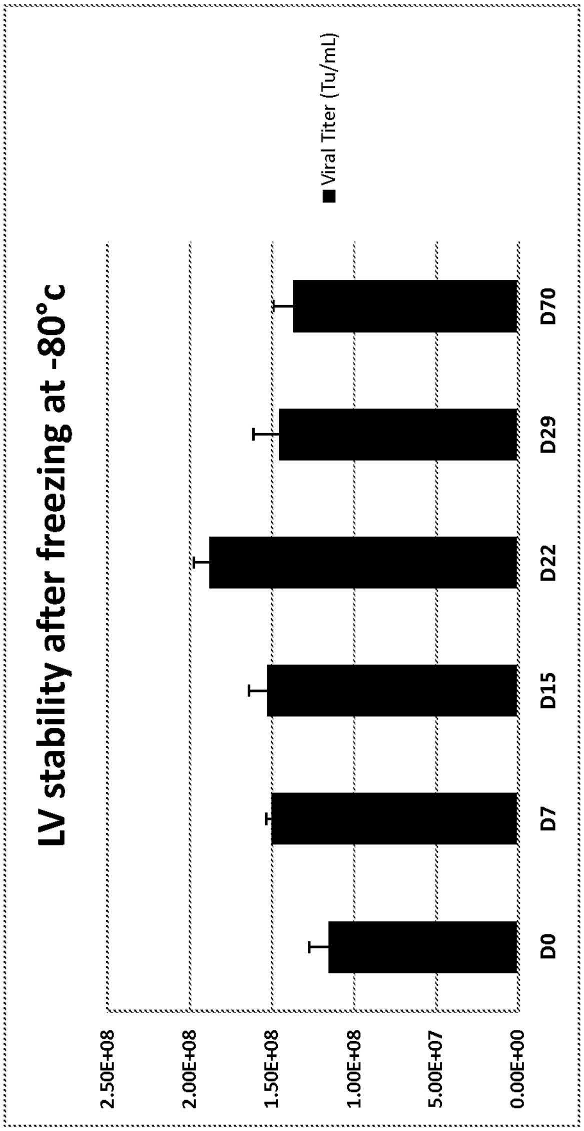
FIG. 2. Viral Vector stability at −80° C. UFT fractions obtained after Ultrafiltration/Diafiltration were aliquoted in 2R vials. Vials were frozen at −80° C. for at least 24 hrs. Then, at indicated times, samples were thawed at +4° C. and titrated to check the effect of the freezing process in vector bioactivity. Studies were performed for a period of up to 70 days.

In a second experiment lentiviral particle suspensions were frozen in Tris buffer as before but were then stored for 7, 15, 22, 29, and 70 days before thawing and measuring of the infectious titer. As shown in FIG. 2, long term storage (up to 70) days in Tris buffer did not impact viral titer.

Figure 3:
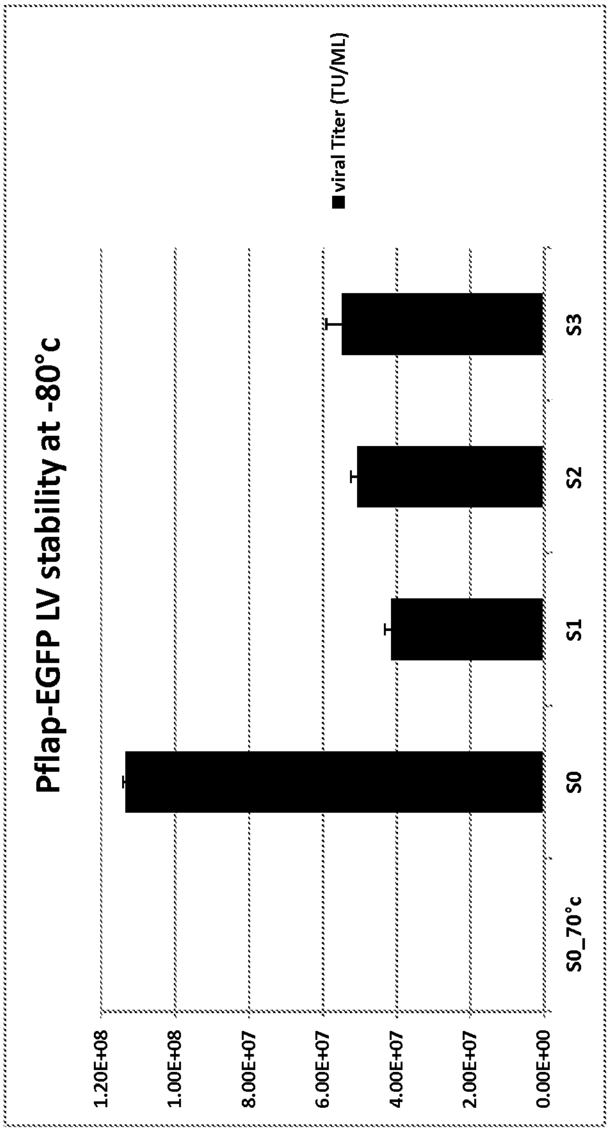
FIG. 3. Effect of sugars during Lentiviral Vector Freezing at −80° C. Purified and concentrated viral vector were frozen at −80° C., in absence and in presence of sugars (Sucrose or Trehalose). 24 h after freezing, samples were quickly thawed at +4° C. and then titrated to check the effect of the sugars on vector bioactivity during freezing process.

A third experiment compared three different buffer solutions. S1 is Tris buffer; S2 is Tris buffer containing 0.5M sucrose; and S3 is Tris buffer containing 0.5 M trehalose. As shown in FIG. 3, freezing reduced the viral titer by an approximately equal amount in each of S1, S2, and S3 buffer as compared to the starting viral suspension (S0 in the figure). However, the three buffers and in particle the two containing sugar had very little if any impact on viral titer after freezing.

Taken together, these data indicate that lentiviral particles retain infectious titer when frozen.

Example 5

Stability of Lyophilized Lentiviral Vector Particles

In a first experiment lentiviral particle suspensions in buffers S1, S2, and S3 were prepared and frozen at −80° C. for at least 16 hours and then freeze dried in Alpha 1-2 bouchage for 18-22 hrs.

Each sample condition was performed in duplicates.

Figure 4:
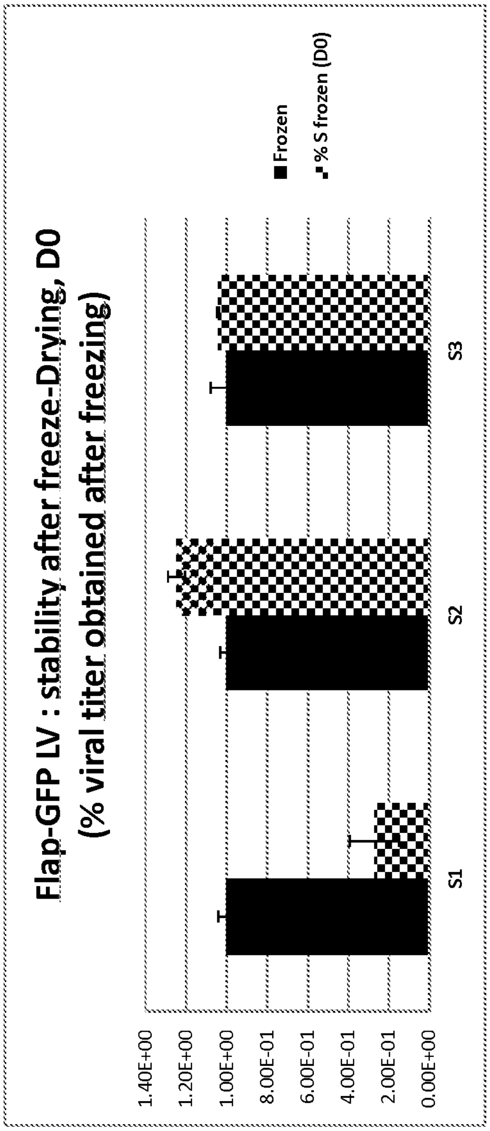
FIG. 4. Stability of Lentiviral Vector immediately after Freeze-Drying: effect of sugars (Sucrose & Trehalose). Purified and concentrated viral vector were frozen at −80° C. for 24 hours, in absence and in presence of sugars (Sucrose or Trehalose) in Tris buffer (20 mM Tris pH 7.6/$MgCl_2$ 2 mM). Then frozen samples were lyophilized at −55° C. and 0.02 mbar for 18 hrs in Christ Alpha 1-2D plus Freeze-Dryer.

The frozen samples were thawed and the freeze dried samples were reconstituted by adding a volume of Dnase-Rnase free water equal to the initial volume of viral suspension before freezing) in the vial containing freeze dried product. Then vials were vortexed to solubilize the freeze dried product. Viral titers were then measured for each frozen and each lyophilized sample. The viral titer of the freeze dried sample was then compared to the titer of the frozen sample in the same buffer. The data are presented in FIG. 4. For each buffer condition the frozen sample viral titer is normalized to 1.00 and the titer of the lyophilized sample is presented relative to that value. As shown, lyophilization in S1 resulted in a loss of viral titer of over 75%. In contrast, lyophilization in buffers S2 and S3 did not result in any loss of titer.

Figure 5:
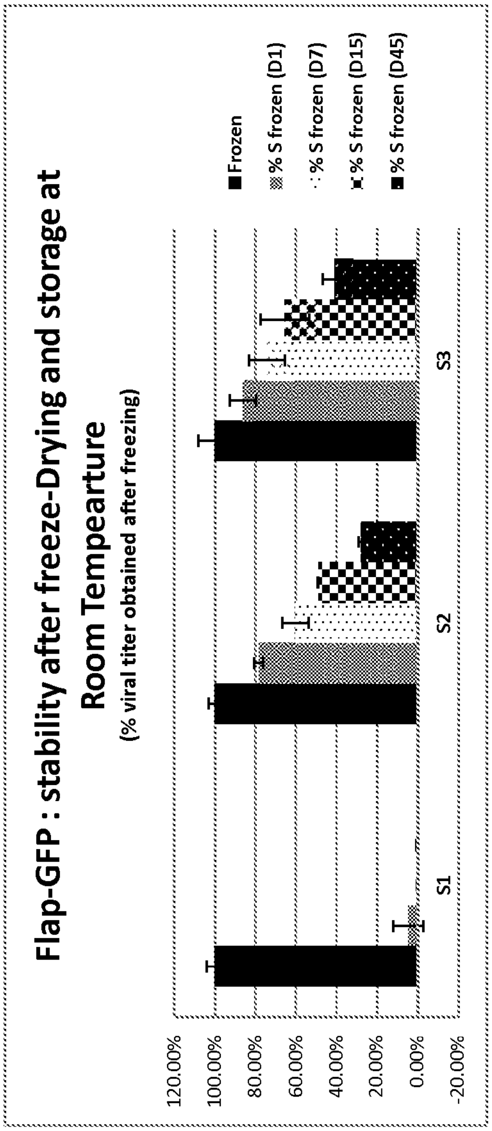
FIG. 5. Storage of Lentiviral Vector at room temperature after Freeze-Drying: effect of sugars (Sucrose & Trehalose). Purified and concentrated viral vector were frozen at −80° C., in absence and in presence of sugars (Sucrose or Trehalose) were frozen for 24 hrs in Tris buffer (20 mM Tris pH 7.6/$MgCl_2$ 2 mM). Then frozen samples were lyophilized at −55° C. and 0.02 mbar for 18 hrs in Christ Alpha 1-2D plus Freeze-Dryer. At the end of the lyophilization process, vials were manually closed, sealed and stored in the dark at room temperature (22-25° C.). At the indicated times, samples were reconstituted and titrated to evaluate the effect of the lyophilization process on vector stability. Studies were performed for a period of up to 45 days.

In a second experiment, lentiviral vector suspensions were frozen or were freeze dried as before and then stored at room temperature for 1, 7, 15, or 45 days. As shown in FIG. 5, storing at room temperature in the absence of sugar resulted in a very rapid loss of viral titer. The titer is reduced by over 95% after 1 day and is almost undetectable after 7 days. In contrast, freeze drying in the presence of the sugars dramatically reduces the rate of loss of viral titer. (Each bar in the graph in FIG. 5 represents two data points.)

Figure 6:
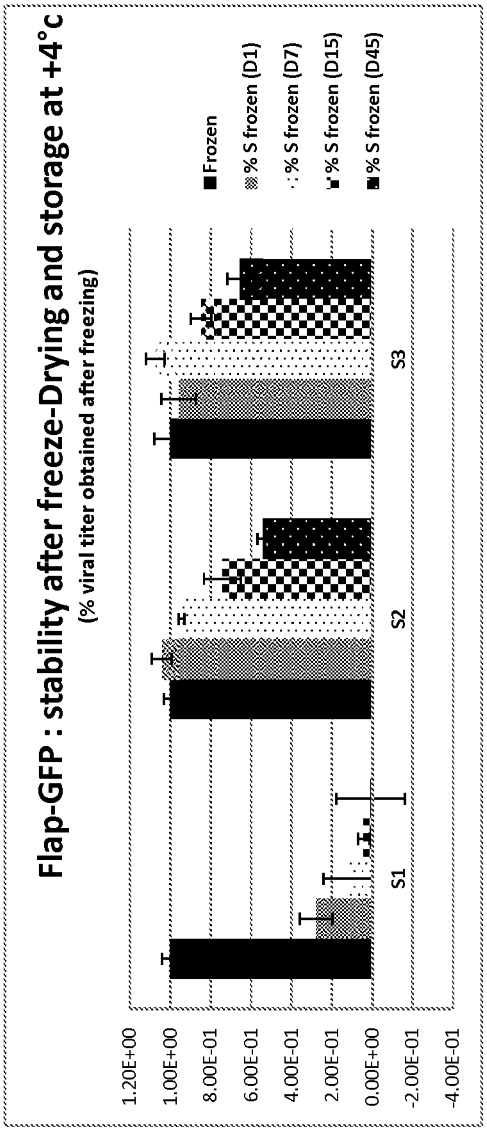
FIG. 6. Storage of Lentiviral Vector in the fridge (+4° C.) after Freeze-Drying: effect of sugars (Sucrose & Trehalose). Purified and concentrated lentiviral vector particles were frozen at −80° C. for 24 hours, in absence and in presence of sugars (Sucrose or Trehalose) in Tris buffer (20 mM Tris pH 7.6/$MgCl_2$ 2 mM). Then frozen samples were lyophilized at −55° C. and 0.02 mbar for 18 hrs in Christ Alpha 1-2D plus Freeze-Dryer. At the end of the lyophilization process, vials were manually closed, sealed and stored in the dark at +4° C. At the indicated times, samples were reconstituted and titrated to evaluate the effect of the lyophilization process on vector stability. Studies were performed for a period of up to 45 days.

In a third experiment, lentiviral vector suspensions were frozen or were freeze dried as before and then stored at +4° C. for 1, 7, 15, or 45 days. As shown in FIG. 6, storing at +4° C. in the absence of sugar resulted in a very rapid loss of viral titer. The titer is reduced by over 70% after 1 day and over 95% after 15 days. In contrast, freeze drying in the presence of the sugars dramatically reduces the rate of loss of viral titer. (Each bar in the graph in FIG. 5 represents two data points.)

Figure 7:
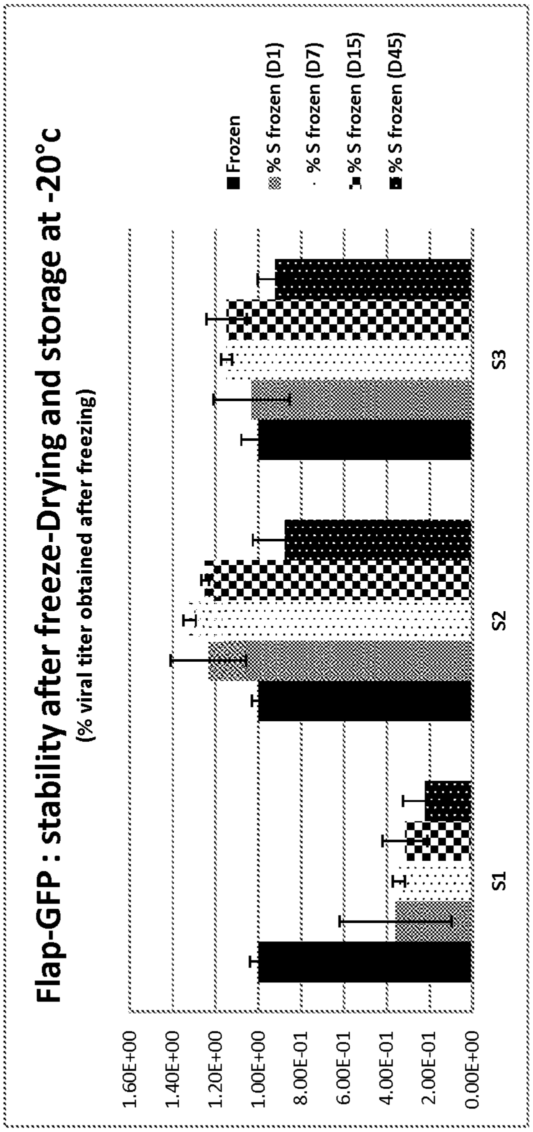
FIG. 7. Storage of Lentiviral Vector at −20° C. after Freeze-Drying:effect of sugars (Sucrose & Trehalose). Purified and concentrated lentiviral vector particles were frozen at −80° C. for 24 hours, in absence and in presence of sugars (Sucrose or Trehalose) in Tris buffer (20 mM Tris pH 7.6/$MgCl_2$ 2 mM). Then frozen samples were lyophilized at −55° C. and 0.02 mbar for 18 hrs in Christ Alpha 1-2D plus Freeze-Dryer. At the end of the lyophilization process, vials were manually closed, sealed and stored in the dark at −20° C. At the indicated times, samples were reconstituted and titrated to evaluate the effect of the lyophilization process on vector stability. Studies were performed for a period of up to 45 days.

In a fourth experiment, lentiviral vector suspensions were frozen or were freeze dried as before and then stored at −20° C. for 1, 7, 15, or 45 days. As shown in FIG. 7, storing at −20° C. in the absence of sugar resulted in a rapid loss of viral titer. The titer is reduced by over 60% after 1 day and almost 80% after 45 days. In contrast, freeze drying in the presence of the sugars dramatically reduces the rate of loss of viral titer. (Each bar in the graph in FIG. 5 represents two data points.) Storing at −20° C. resulted in a retention of over 80% of the viral titer for up to 45 days and in no loss of viral titer for up to 15 days in the samples that were freeze dried in the presence of 0.5M sugar.

Example 6

Comparison of Different Lyoprotectants

Figure 8:
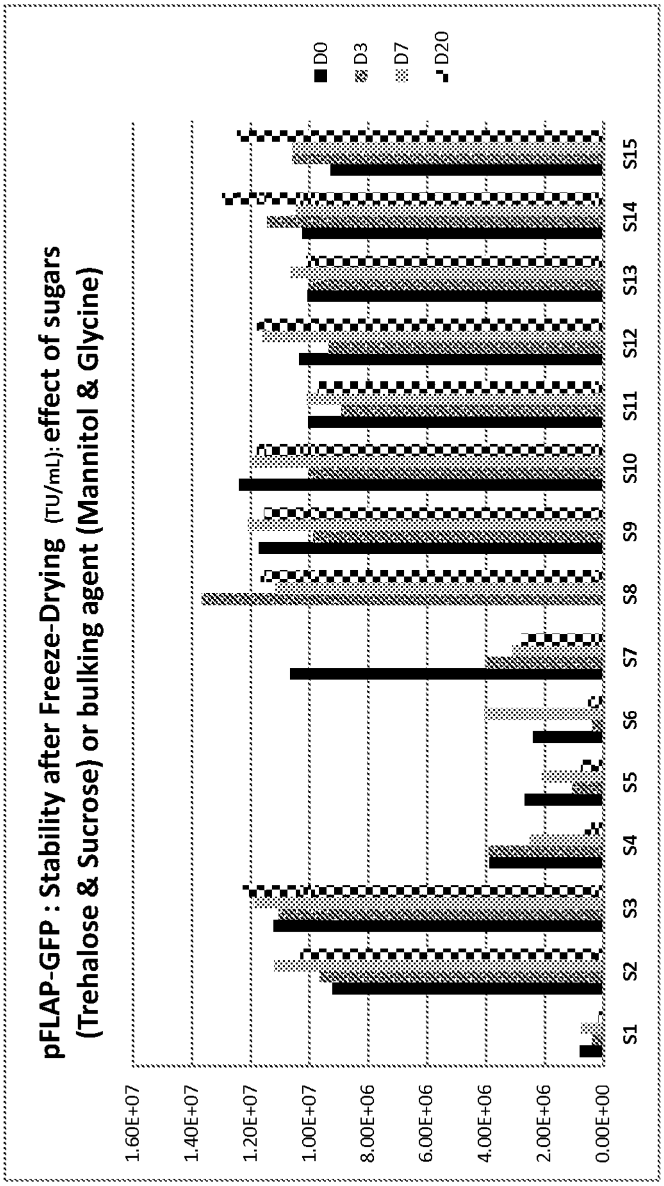
FIG. 8. Stability of Lentiviral Vector at −20° C. after Freeze-Drying: effect of sugars (Sucrose & Trehalose) or bulking agents (Mannitol & Glycine). Comparison of freeze drying in absence (S1) and in presence of Sucrose 0.5 M (S2), Trehalose 0.5 M (S3), Mannitol 0.8% (S4), Mannitol 0.4% (S5), Glycine 0.8% (S6), Glycine 0.4% (S7), Sucrose+Mannitol 0.8% (S8), Sucrose+Mannitol 0.4% (S9), Sucrose+Glycine 0.8% (S10), Sucrose +Glycine 0.4% (S11), Trehalose+Mannitol 0.8% (S12), Trehalose+Mannitol 0.4% (S13), Trehalose+Glycine 0.8% (S14), Trehalose+Glycine 0.4% (S15) for 24 hrs in Tris buffer (20 mM Tris pH 7.6/$MgCl_2$ 2 mM).

In this experiment different lyoprotectants were compared. Purified and concentrated viral vectors were frozen at −80° C., in absence (S1) and in presence of Sucrose 0.5 M (S2), Trehalose 0.5 M (S3), Mannitol 0.8% (S4), Mannitol 0.4% (S5), Glycine 0.8% (S6), Glycine 0.4% (S7), Sucrose+Mannitol 0.8% (S8), Sucrose+Mannitol 0.4% (S9), Sucrose+Glycine 0.8% (S10), Sucrose+Glycine 0.4% (S11), Trehalose+Mannitol 0.8% (S12), Trehalose+Mannitol 0.4% (S13), Trehalose+Glycine 0.8% (S14), Trehalose+Glycine 0.4% (S15) for 24 hrs in Tris buffer (20 mM Tris pH 7.6/$MgCl_2$ 2 mM). Then frozen samples were lyophilized at −55° C. and 0.02 mbar for 18 hrs in Christ Alpha 1-2D plus Freeze-Dryer. At the end of the lyophlization process, vials were manually closed, sealed and stored in the dark at −20° C. At the indicated times (day 0, day 3, day 7, and day 20) samples were reconstituted and titrated to evaluate the effect of sugars or bulking agent on stability of viral vector. The results are shown in FIG. 8.

Example 7

Low Serum Lentiviral Vector Particle Production

The production protocol described in Example 1 utilizes production medium comprising 2% non-human serum. For lentiviral pharmaceutical applications it would be useful to prepare and freeze dry lentiviral vector particles in the absence of non-human serum and/or in the presence of less than 0.5% serum. This example describes an experimental protocol designed to characterize lentiviral vector particle production under such conditions.

The same protocol outlined in Example 1 was followed, except that 18 to 24 hours post-transfection, culture medium was changed with either of two alternative production mediums. Production medium 1 corresponded to Dulbecco's modified Eagle's medium (DMEM/High modified, Hyclone) supplemented with 2% heat-inactivated fetal calf serum (FCS, PAA), 1% L-Glutamine (Gibco by Life technologies), 1% Penicillin-Streptomycin (Gibco by Life technologies), 1% Sodium Pyruvate (Gibco by Life technologies), BENZONASE® (pharma grade I, 100 000U, Merck Millipore) and MgCL2 1M. Production medium 2 corresponded to Dulbecco's modified Eagle's medium (DMEM/High modified, Hyclone) supplemented with 2% heat-inactivated fetal calf serum (FCS, PAA), 1% L-Glutamine (Gibco by Life technologies), 1% Penicillin-Streptomycin (Gibco by Life technologies), 1% Sodium Pyruvate (Gibco by Life technologies), BENZONASE® (pharma grade I, 100 000U, Merck Millipore) and MgCL2 1M. Thus, the only difference between the media is that production medium 1 contains 2% FCS while production medium 2 does not contain serum. Because of the serum present in the culture medium, however, some residual FCS (less than 0.5%) is present in the culture grown in production medium 2. The lentiviral vector particles were then purified and concentrated as described in Example 1.

Example 8

Lyophilization of Lentiviral Vector Particles in the Presence of a Low Serum Concentration The purified and concentrated lentiviral vector particles produced according to Example 7 were diluted 1:2 in Tris (PBS) buffer with and without 0.5 M sucrose. The lentiviral vector particle stocks were then frozen and −80 C and lyophilized. Infectious titres, DNA, host cell proteins, and BSA were measured after freezing but before lyophilization, and after lyophilization. The results are presented in Table 4.

TABLE 4

| UF | | 0% BSA Tris | | 0% BSA Tris + Sucrose 0.5M | | 2% BSA Tris | | 2% BSA Tris + Sucrose 0.5M | |
|---|---|---|---|---|---|---|---|---|---|
| Test | Method | Frozen | Lyophilized | Frozen | Lyophilized | Frozen | Lyophilized | Frozen | Lyophilized |
| Infectious Titre | PCR | Fail | Fail | Fail | Fail | $1.19 \times 10^7$ | Fail | $1.60 \times 10^7$ | $5.65 \times 10^7$ |
| Total DNA | Picogreen ng/ml | | 0 | 1.87 | 24.21 | 46.67 | 749.17 | 103.51 | 736.78 |
| Post Cell Proteins HEK293 | PCP HEK293 ELISA ng/ml | 6.44 | 214.46 | 87.66 | 299.58 | 272.87 | 1748.08 | 506.37 | 5739.25 |
| Residual BSA | SA Residual ELISA ng/ml | 897.61 | 5219.12 | 923.52 | 6053.22 | 2904.88 | 18357.55 | 5894.15 | 41173.62 |

The culture grown in 2% serum contains many more cells than the culture grown in 0% serum because cell growth ceases when the cells are transferred out of serum (data not shown). That is reflected in the levels of contaminating DNA and HEK293 host cell proteins reported in Table 4. In this experiment the transductions failed for several samples so it was not possible to measure the viral titre.

Example 9

Effect of Lyophilization on T-cell Specific Responses to Lentiviral Vector Particles In this experiment the ability of the lyophilized lentiviral vector particles to induce T-cell specific responses was analyzed. Seven groups of five mice were analyzed as described in Tables 5 and 6. The lentiviral vector particles used are those produced according to Example 7 and having the properties described in Example 8.

Cumulative T cell specific response (IFN-gamma secretion) of the lentiviral particles was determined in C57Bl/6j mice.

TABLE 5

| Group | Vector | Dose (TU/mouse) | N° of animals |
|---|---|---|---|
| 1 | 2% BSA/Tris/Frozen | 5.10e6 | 5 F |
| 2 | 2% BSA/Tris/Frozen | 5.10e5 | 5 F |
| 3 | 2% BSA/Tris + Sucrose 0.5M/Frozen | 5.10e6 | 5 F |
| 4 | 2% BSA/Tris + Sucrose 0.5M/Frozen | 5.10e5 | 5 F |
| 5 | % BSA/Tris + Sucrose 0.5M/Lyophilized | 5.10e6 | 5 F |
| 6 | % BSA/Tris + Sucrose 0.5M/Lyophilized | 5.10e5 | 5 F |
| 7 | Tris Buffer | NA | 5 F |

TABLE 6

| Name of peptide | Sequence | Localisation | Restriction |
|---|---|---|---|
| Q-15-W | QMVHQAISPR TLNAW | P24 (pool DG) | CMH II |
| Y-15-N | YKTLRAEQAS QEVKN | P24 (pool HG) | CMH II |
| E-15-Q | EAMSQVTNSA TIMMQ | NC (pool JG) | CMH I |
| K-15-P | KYTAFTIPSIN NETP | POL (pool AP) | ND |

Figure 9:
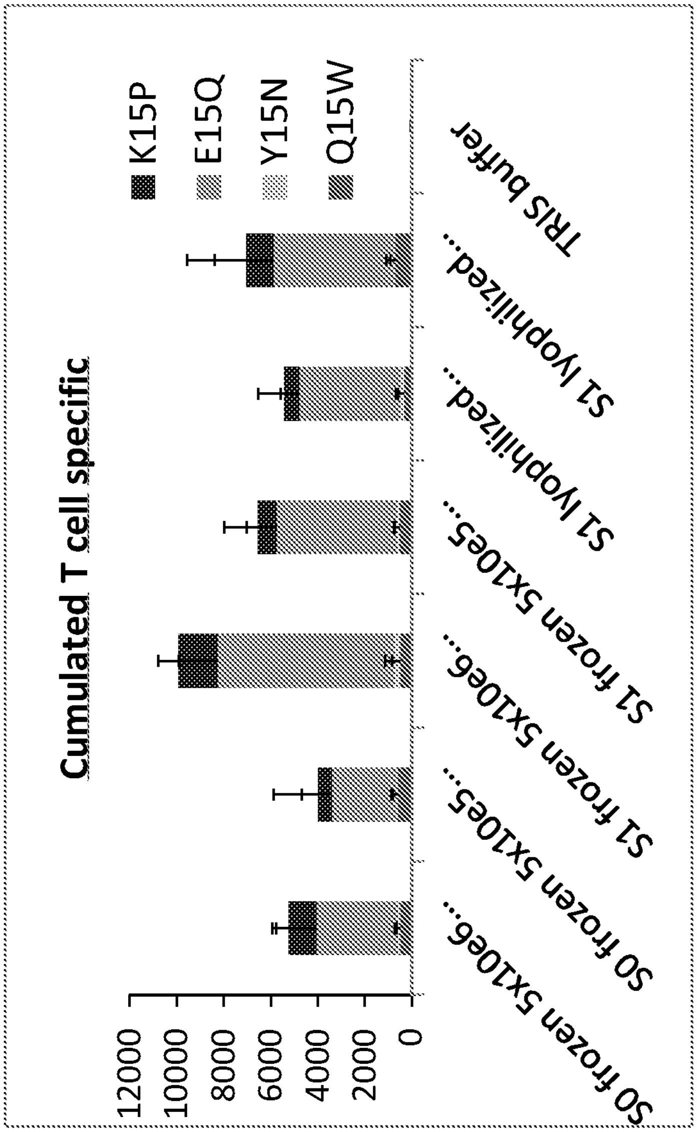
FIG. 9. Cumulative T Cell Specific Response (IFN-gamma secretion) in C57Bl/6j Mice Cumulative T cell specific response (IFN-gamma secretion) of the lentiviral particles was determined in C57Bl/6j mice.

The results, shown in FIG. 9, demonstrate that the lyophilized lentiviral vector particle vaccine has an equivalent immunologic effect compared to its frozen version with or without sucrose.

Example 10

Figure 10:
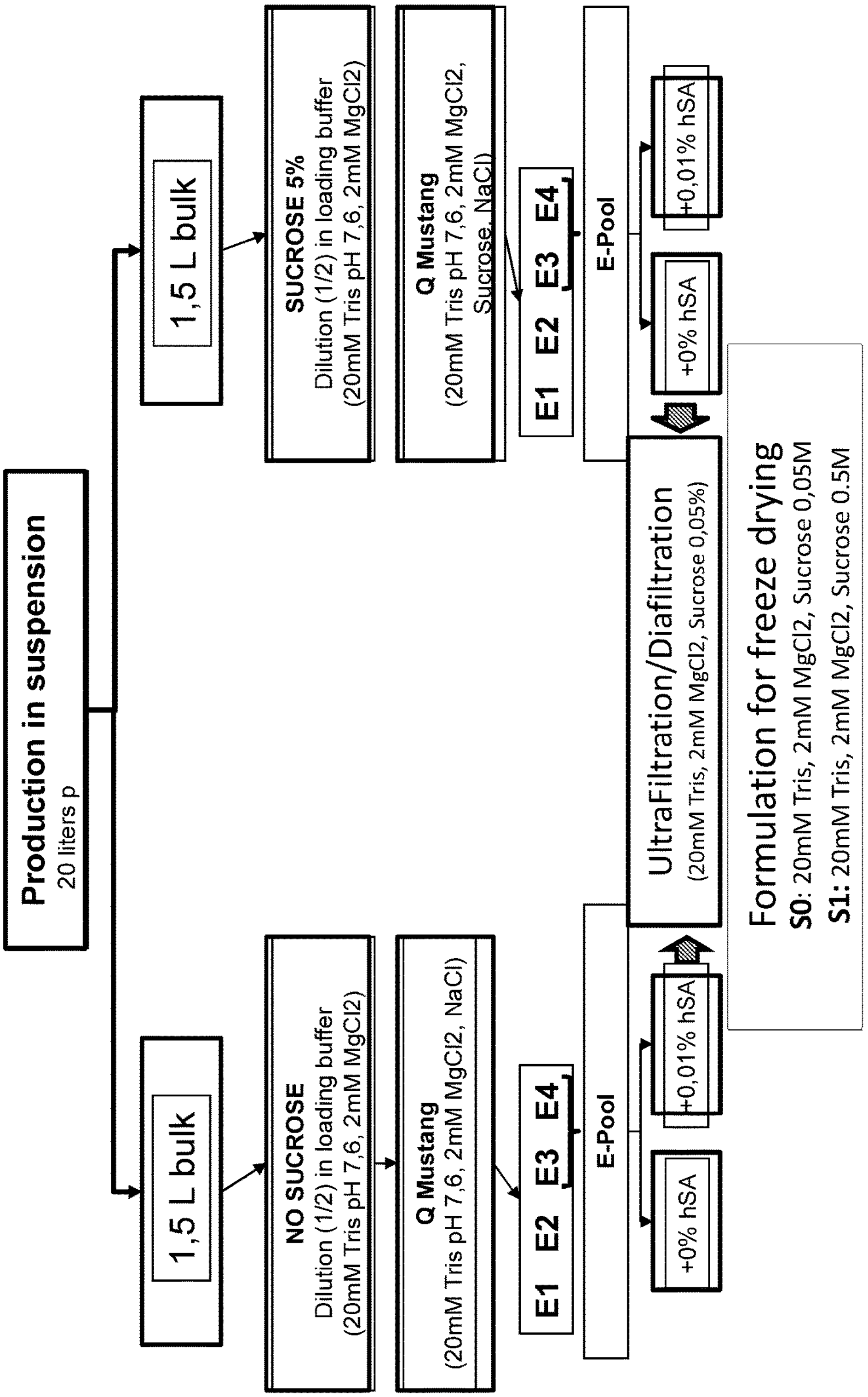
FIG. 10. Flow chart for purificationand concentration of lentiviral vectors. The procedure for purification and concentration of lentiviral vectors is depicted. Cells were grown in the absence of serum in synthetic medium. The procedure was performed in the presence o absence of 5% (final) sucrose. The elution concentrations were E1: 0.15 M NaCl; E2: 0.3 M NaCl; E3: 0.5 M NaCl; and E4: 1.2 M NaCl. E3/E4 fractions were pooled and 0% or 0.01% human serum albumin (HSA) was added.
Figure 11:
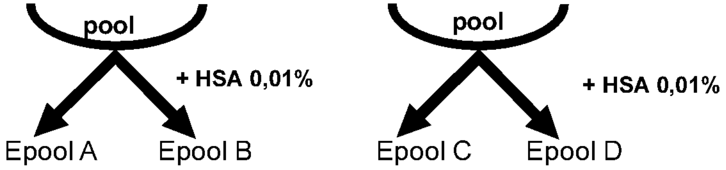
FIG. 11. Recoveries before and after purification. Infectious titers were determined in the bulk samples and in the Epool, after purification. Sucrose had little effect on the recoveries.

Lyophilization of Lentiviral Vector Particles in the Presence of a Defined Very Low Concentration of Serum Lentiviruses were produced from cells grown in serum-free suspention cultures in defined medium. Lentiviruses were purified and concentrated as shown in FIG. 10 with or without added sucrose.

Following purification and concentration, the purified and concentrated lentiviral vector particles were dilted 1:2 in Tris (PBS) buffer with and without 0.5 M sucrose. The lentiviral vector particle stocks were then frozen and −80 C and lyophilized. Infectious titres, DNA, host cell proteins, and BSA were measured after freezing and before lyophilization, and after lyophilization. The results are presented in Table 7.

TABLE 7

| UF | | Tris | | Tris + Sucrose 0.5M | |
|---|---|---|---|---|---|
| Test | Method | Frozen | Lyophilized | Frozen | Lyophilized |
| Infectious titer | qPCR | 1.02E+07 | 1.03E+07 | 1.10E+07 | 1.04E+07 |
| Total DNA | Picogreen ng · $mL^{-1}$ | — | 63.7 | — | 57.6 |
| Residual hSA | hSA RESID ELISA mg/mL | 4.360 | 4.075 | 3.025 | 4.055 |

The results demonstrate high and clinically useful titres of lentiviral vector particles obtained following production of viral particles in suspension culture in the absense of non-human serum.

Example 11

Effect of Serum and Sucrose Concentration of Lentiviral Vector Particle Stability The influence of sucrose and hSA on lentiviral particle stability during purification and lyophilization was assessed according to the procedures in FIG. 10. The results are shown in FIGS. 11-14. Infectious titers were determined in the bulk samples and in the Epool, after purification. Sucrose had little effect on the recoveries. Infectious titers were determined in frozen vs. frozen and lyophilized samples+/−sucrose and +/−HSA. Neither sucrose nor HAS had a large effect on the recoveries.

While the present teachings are described in conjunction with various embodiments, it is not intended that the present teachings be limited to such embodiments. On the contrary, the present teachings encompass various alternatives, modifications and equivalents, as will be appreciated by those of skill in the art. Thus, the invention as contemplated by applicants extends to all functionally equivalent structures, methods and uses, such as are within the scope of the appended claims.

Moreover, in the following claims it should be understood that the order of steps or order for performing certain actions (e.g. mixing of reactants) is immaterial so long as the present teachings remain operable. Unless expressly stated otherwise or where performing the steps of a claim in a certain order would be non-operative, the steps and/or substeps of the following claims can be executed in any order. Moreover, two or more steps or actions can be conducted simultaneously.

We claim:

1. A method for making lyophilized lentiviral vector particles, the method comprising:

a) providing a cell supernatant comprising lentiviral vector particles, b) purifying the lentiviral vector particles in the supernatant, c) concentrating the purified lentiviral vector particles, d) freezing the concentrated lentiviral vector particles to provide frozen lentiviral vector particles, e) lyophilizing the frozen lentiviral vector particles in the presence of one or more sugars to provide lyophilized lentiviral vector particles, and f) storing the lyophilized lentiviral vector particles for at least three days, wherein the lyophilized lentiviral vector particles retain at least 80% of their titer after freezing viral titer when stored for 45 days at −20° C.

2. The method of claim 1, wherein the provided cell supernatant does not comprise serum albumin.

3. The method of claim 1, wherein the concentrated lentiviral vector particles are frozen in the presence of no more than 0.1% non-human serum albumin, in particular in the presence of no more than 0.01% non-human serum albumin, in particular in the absence of non-human serum albumin.

4. The method of claim 1, wherein the concentrated lentiviral vector particles are frozen in the presence of no more than 0.1% serum albumin, preferably in the presence of no more than 0.01% serum albumin.

5. The method of claim 1, wherein the concentrated lentiviral vector particles produced in c) comprise no more than 1 μg total DNA per $1\times10^8$ TU.

6. The method of claim 1, wherein the concentrated lentiviral vector particles produced in c) comprise no more than 20 μg of serum albumin per $1\times10^8$ TU.

7. The method of claim 1, wherein the purifying in b) comprises clarifying the cell supernatant of a), and wherein the amount of total DNA per TU present in the concentrated lentiviral vector particles produced in c) is no more than 20% of the amount of total DNA per TU present in the cell supernatant.

8. The method of claim 1, wherein the purifying in b) comprises clarifying the cell supernatant of a), and wherein the amount of total protein per TU present in the concentrated lentiviral vector particles produced in c) is no more than 1% of the amount of total protein per TU present in the cell supernatant.

9. The method of claim 1, wherein the purifying in b) comprises clarifying the cell supernatant of a), and wherein the amount of host cell proteins per TU present in the concentrated lentiviral vector particles produced in c) is no more than 1% of the amount of total host cell proteins per TU present in the cell supernatant.

10. The method of claim 1, wherein the purifying of step b) comprises two separate treatments with endonuclease from *Serratia marcescens*.

11. The method of claim 10, wherein the two treatments with endonuclease from *Serratia marcescens* are performed on the cell supernatant and are followed by clarification of the supernatant by filtration.

12. The method of claim 11, wherein the purifying of step b) further comprises a treatment of the clarified supernatant with endonuclease from *Serratia marcescens*.

13. The method of claim 1, wherein the product of step c) is filtered using a filter having a cutoff of 0.2 μm.

14. The method of claim 1, wherein the product resulting from step c) is suitable for clinical use.

15. The method of claim 1, wherein the purifying of step b) comprises a two-step elution from an anion exchanger, the first step comprising elution at a first salt concentration, and the second step comprising elution at a second salt concentration, the second salt concentration being higher than the first.

16. The method of claim 15, wherein the first salt concentration is 0.5M NaCl and the second salt concentration is 1.2M NaCl.

17. The method of claim 15, wherein the fraction eluted at the first salt concentration and the fraction eluted at the second salt concentration are both diluted to 150 mM NaCl concentration and then combined.

18. The method of claim 1, wherein the lyophilizing of step e) is performed in the presence of one or more sugars at a total concentration of at least 0.5M.

19. The method of claim 18, wherein the one or more sugars comprise sucrose or trehalose.

20. The method of claim 1, wherein the lyophilizing of step e) is performed in the presence of Tris buffer.

21. A method of administering a lentiviral particle to a human subject, comprising:

a) making lyophilized lentiviral vector particles by a method comprising:

i) providing a cell supernatant comprising lentiviral vector particles, ii) purifying the lentiviral vector particles in the supernatant, iii) concentrating the purified lentiviral vector particles, iv) freezing the concentrated lentiviral vector particles to provide frozen lentiviral vector particles, v) lyophilizing the frozen lentiviral vector particles in the presence of one or more sugars to provide lyophilized lentiviral vector particles, and vi) storing the lyophilized lentiviral vector particles for at least three days, wherein the lyophilized lentiviral vector particles retain at least 80% of their titer after freezing viral titer when stored for 45 days at -20° C.;

b) reconstituting the lyophilized lentiviral vector particles in an aqueous medium for administration; and c) administering the reconstituted lentiviral vector particles to the human subject.

22. The method of claim 21, wherein the provided cell supernatant does not comprise non-human serum albumin.

23. The method of claim 21, wherein the concentrated lentiviral vector particles are frozen in the presence of no more than 0.1% nonhuman serum albumin, in particular no more than 0.01% serum albumin.

24. The method according to claim 21, wherein the lyophilized lentiviral vector particles comprise no more than 20 μg of serum albumin per $1\times10^8$ TU of lentiviral vector particles in the composition.

25. The method according to claim 21, wherein the lyophilized lentiviral vector particles do not comprise non-human serum albumin.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer Flap A

<400> SEQUENCE: 1

cccaagaacc caaggaaca                                                    19


<210> SEQ ID NO 2
<211> LENGTH: 25
<212> TYPE: DNA
<213> ORGANISM: Artificial Sequence
<220> FEATURE:
<223> OTHER INFORMATION: Synthetic Primer Flap S

<400> SEQUENCE: 2

agacaagata gaggaagagc aaaac                                             25


<210> SEQ ID NO 3
<211> LENGTH: 27
<212> TYPE: DNA
<213> ORGANISM: Artificial Sequence
<220> FEATURE:
<223> OTHER INFORMATION: Synthetic Lenti TM probe

<400> SEQUENCE: 3

aaccattagg agtagcaccc accaagg                                           27


<210> SEQ ID NO 4
<211> LENGTH: 24
<212> TYPE: DNA
<213> ORGANISM: Artificial Sequence
<220> FEATURE:
<223> OTHER INFORMATION: Synthetic Actine A primer

<400> SEQUENCE: 4

cggtgaggat cttcatgagg tagt                                              24


<210> SEQ ID NO 5
<211> LENGTH: 20
<212> TYPE: DNA
<213> ORGANISM: Artificial Sequence
<220> FEATURE:
<223> OTHER INFORMATION: Synthetic Actine S primer

<400> SEQUENCE: 5

aacaccccag ccatgtacgt                                                   20


<210> SEQ ID NO 6
<211> LENGTH: 22
<212> TYPE: DNA
<213> ORGANISM: Artificial Sequence
<220> FEATURE:
<223> OTHER INFORMATION: Synthetic HUMURA ACT TM probe

<400> SEQUENCE: 6

ccagccaggt ccagacgcag ga                                                22
```